US012573516B2

(12) United States Patent
Nunn

(10) Patent No.: US 12,573,516 B2
(45) Date of Patent: Mar. 10, 2026

(54) RADIOISOTOPE GENERATOR EARLY BREAKTHROUGH DETECTION

(71) Applicant: BRACCO DIAGNOSTICS INC., Monroe Township, NJ (US)

(72) Inventor: Adrian Nunn, Lambertville, NJ (US)

(73) Assignee: BRACCO DIAGNOSTICS INC., Monroe Township, NJ (US)

( * ) Notice: Subject to any disclaimer, the term of this patent is extended or adjusted under 35 U.S.C. 154(b) by 878 days.

(21) Appl. No.: 17/799,767

(22) PCT Filed: Feb. 19, 2021

(86) PCT No.: PCT/US2021/018807
§ 371 (c)(1),
(2) Date: Aug. 15, 2022

(87) PCT Pub. No.: WO2021/168272
PCT Pub. Date: Aug. 26, 2021

(65) Prior Publication Data
US 2023/0084501 A1 Mar. 16, 2023

Related U.S. Application Data

(60) Provisional application No. 62/979,886, filed on Feb. 21, 2020.

(51) Int. Cl.
*G21G 1/00* (2006.01)
*A61M 5/00* (2006.01)
(Continued)

(52) U.S. Cl.
CPC ........... *G21G 1/0005* (2013.01); *A61M 5/007* (2013.01); *A61M 5/142* (2013.01); *A61M 2205/18* (2013.01)

(58) Field of Classification Search
CPC ..... G21G 1/0005; A61M 5/007; A61M 5/142; A61M 2205/18
See application file for complete search history.

(56) References Cited

U.S. PATENT DOCUMENTS

| | | | |
|---|---|---|---|
| 3,483,867 | A | 12/1969 | Markovitz |
| 3,535,085 | A | 10/1970 | Shumate |

(Continued)

FOREIGN PATENT DOCUMENTS

| | | |
|---|---|---|
| AT | 399241 B | 4/1995 |
| CA | 2913373 A1 | 4/2008 |

(Continued)

OTHER PUBLICATIONS 337-1110_662084: Complainant Bracco Diagnostics Inc.'s Response to Jubilant's Motion for Summary Determination of Noninfringement of U.S. Pat. No. 9,750,869, U.S. Pat. No. 9,750,870, and U.S. Pat. No. 9,814,826 by Jubilant's Version 3.1 and Version 4 Designs and Memorandum in Support Thereof (Motion Response/Reply); 2-1386970: "Disputes to Chart of Material Facts", create date Nov. 19, 2018, www.edis.usitc.gov.

(Continued)

*Primary Examiner* — Nicole M Ippolito
(74) *Attorney, Agent, or Firm* — Fredrikson & Byron, P.A.

(57) ABSTRACT

An infusion system can include a radioisotope generator that generates a radioactive eluate via an elution, an activity detector configured to measure an activity of the radioactive eluate generated by the radioisotope generator, and a controller. The controller can analyze a radioactivity profile of the radioactive eluate to determine a characteristic of the profile indicative of breakthrough. The controller may issue a user alert, cease elution, or perform yet other actions based on the analysis.

20 Claims, 8 Drawing Sheets

(51) Int. Cl.
    *A61M 5/14*         (2006.01)
    *A61M 5/142*      (2006.01)

(56)            References Cited

U.S. PATENT DOCUMENTS

| | | | |
|---|---|---|---|
| 3,543,752 | A | 12/1970 | Hesse et al. |
| 3,565,376 | A | 2/1971 | Viers |
| 3,576,998 | A | 5/1971 | Deutsch et al. |
| 3,710,118 | A | 1/1973 | Holgate et al. |
| 3,714,429 | A | 1/1973 | Mozley et al. |
| 3,767,915 | A | 10/1973 | Battist |
| 3,774,036 | A | 11/1973 | Gerhart |
| 3,847,138 | A | 11/1974 | Gollub |
| 3,861,380 | A | 1/1975 | Chassagne |
| 3,953,567 | A | 4/1976 | Grant et al. |
| 3,991,960 | A | 11/1976 | Tanaka |
| 3,997,784 | A | 12/1976 | Picunko et al. |
| 4,096,859 | A | 6/1978 | Agarwal et al. |
| 4,160,910 | A | 7/1979 | Thornton et al. |
| 4,212,303 | A | 7/1980 | Nolan |
| 4,239,970 | A | 12/1980 | Eckhardt et al. |
| 4,241,728 | A | 12/1980 | Mirell |
| 4,286,169 | A | 8/1981 | Rossem |
| 4,336,036 | A | 6/1982 | Leeke et al. |
| 4,406,877 | A | 9/1983 | Neirinckx et al. |
| 4,466,888 | A | 8/1984 | Verkaart |
| 4,562,829 | A | 1/1986 | Bergner |
| 4,585,009 | A | 4/1986 | Barker et al. |
| 4,585,941 | A | 4/1986 | Bergner |
| 4,597,951 | A | 7/1986 | Gennaro et al. |
| 4,623,102 | A | 11/1986 | Hough, Jr. |
| 4,624,661 | A | 11/1986 | Arimond |
| 4,625,118 | A | 11/1986 | Kriwetz et al. |
| 4,656,697 | A | 4/1987 | Naeslund |
| 4,674,403 | A | 6/1987 | Bryant et al. |
| 4,679,142 | A | 7/1987 | Lee |
| 4,755,679 | A | 7/1988 | Wong |
| 4,759,345 | A | 7/1988 | Mistry |
| 4,769,008 | A | 9/1988 | Hessel |
| 4,847,505 | A | 7/1989 | Suthanthiran |
| 4,853,546 | A | 8/1989 | Abe et al. |
| 4,859,431 | A | 8/1989 | Ehrhardt |
| 4,994,056 | A | 2/1991 | Ikeda |
| 5,039,863 | A | 8/1991 | Matsuno et al. |
| 5,092,834 | A | 3/1992 | Bradshaw et al. |
| 5,115,407 | A | 5/1992 | Bird et al. |
| 5,166,526 | A | 11/1992 | Dietzel |
| 5,223,434 | A | 6/1993 | Kanno et al. |
| 5,254,328 | A | 10/1993 | Herscheid et al. |
| 5,258,906 | A | 11/1993 | Kroll et al. |
| 5,265,133 | A | 11/1993 | Matthews |
| 5,274,239 | A | 12/1993 | Lane et al. |
| 5,284,481 | A | 2/1994 | Soika et al. |
| 5,395,320 | A | 3/1995 | Padda et al. |
| 5,468,355 | A | 11/1995 | Shefer et al. |
| 5,475,232 | A | 12/1995 | Powers et al. |
| 5,483,070 | A | 1/1996 | Valenta |
| 5,485,831 | A | 1/1996 | Holdsworth et al. |
| 5,573,747 | A | 11/1996 | Lacy |
| 5,580,541 | A | 12/1996 | Wells et al. |
| 5,590,648 | A | 1/1997 | Mitchell et al. |
| 5,674,404 | A | 10/1997 | Kenley et al. |
| 5,681,285 | A | 10/1997 | Ford et al. |
| 5,702,115 | A | 12/1997 | Pool |
| 5,739,508 | A | 4/1998 | Uber, III |
| 5,765,842 | A | 6/1998 | Phaneuf et al. |
| 5,827,429 | A | 10/1998 | Ruschke et al. |
| 5,840,026 | A | 11/1998 | Uber, III et al. |
| 5,885,216 | A | 3/1999 | Evans, III et al. |
| 5,971,923 | A | 10/1999 | Finger |
| 6,058,718 | A | 5/2000 | Forsberg et al. |
| 6,157,036 | A | 12/2000 | Whiting et al. |
| 6,220,554 | B1 | 4/2001 | Daoud |
| 6,267,717 | B1 | 7/2001 | Stoll et al. |
| 6,269,810 | B1 | 8/2001 | Brooker et al. |
| 6,327,895 | B1 | 12/2001 | Jeppsson et al. |
| 6,347,711 | B1 | 2/2002 | Goebel et al. |
| 6,442,418 | B1 | 8/2002 | Evans et al. |
| 6,450,936 | B1 | 9/2002 | Smith et al. |
| 6,454,460 | B1 | 9/2002 | Ramanathan et al. |
| 6,558,125 | B1 | 5/2003 | Futterknecht |
| 6,626,862 | B1 | 9/2003 | Duchon et al. |
| 6,639,237 | B2 | 10/2003 | Pedersen et al. |
| 6,673,594 | B1 | 1/2004 | Owen et al. |
| 6,758,975 | B2 | 7/2004 | Peabody et al. |
| 6,767,319 | B2 | 7/2004 | Reilly et al. |
| 6,773,686 | B1 | 8/2004 | Herscheid et al. |
| 6,787,030 | B2 | 9/2004 | Hsi et al. |
| 6,870,175 | B2 | 3/2005 | Dell et al. |
| 6,901,283 | B2 | 5/2005 | Evans, III et al. |
| 6,908,598 | B2 | 6/2005 | Sylvester |
| 6,931,327 | B2 | 8/2005 | Goode, Jr. et al. |
| 7,091,494 | B2 | 8/2006 | Weisner et al. |
| 7,125,166 | B2 | 10/2006 | Eck et al. |
| 7,163,031 | B2 | 1/2007 | Graves et al. |
| 7,169,135 | B2 | 1/2007 | Duchon et al. |
| 7,204,797 | B2 | 4/2007 | Reilly et al. |
| 7,256,888 | B2 | 8/2007 | Staehr et al. |
| 7,286,867 | B2 | 10/2007 | Schlyer et al. |
| 7,413,123 | B2 | 8/2008 | Ortenzi |
| 7,476,377 | B2 | 1/2009 | Moller et al. |
| 7,504,646 | B2 | 3/2009 | Balestracci et al. |
| 7,522,952 | B2 | 4/2009 | Krieg et al. |
| 7,586,102 | B2 | 9/2009 | Mourtada et al. |
| 7,605,384 | B2 | 10/2009 | Sonnenhol et al. |
| 7,608,831 | B2 | 10/2009 | Lamb et al. |
| 7,612,999 | B2 | 11/2009 | Clark et al. |
| 7,712,491 | B2 | 5/2010 | Tochon-Danguy et al. |
| 7,734,331 | B2 | 6/2010 | Dhawale et al. |
| 7,737,415 | B2 | 6/2010 | Casale et al. |
| 7,780,352 | B2 | 8/2010 | Fox et al. |
| 7,804,415 | B2 | 9/2010 | Cheng et al. |
| 7,813,841 | B2 | 10/2010 | deKemp et al. |
| 7,825,372 | B2 | 11/2010 | Allberg |
| 7,862,534 | B2 | 1/2011 | Quirico et al. |
| 7,996,068 | B2 | 8/2011 | Telischak et al. |
| 8,058,632 | B2 | 11/2011 | Balestracci et al. |
| 8,071,959 | B2 | 12/2011 | deKemp |
| 8,198,599 | B2 | 6/2012 | Bouton et al. |
| 8,216,181 | B2 | 7/2012 | Balestracci |
| 8,216,184 | B2 | 7/2012 | Balestracci |
| 8,295,916 | B2 | 10/2012 | Shimchuk et al. |
| 8,317,674 | B2 | 11/2012 | Quirico et al. |
| 8,431,909 | B2 | 4/2013 | Horton et al. |
| 8,439,815 | B2 | 5/2013 | Lemer |
| 8,442,803 | B2 | 5/2013 | Chen et al. |
| 8,571,881 | B2 | 10/2013 | Rousso et al. |
| 8,615,405 | B2 | 12/2013 | Rousso et al. |
| 8,708,352 | B2 | 4/2014 | Quirico et al. |
| 9,056,164 | B2 | 6/2015 | Tate et al. |
| 9,056,200 | B2 | 6/2015 | Uber, III et al. |
| 9,326,742 | B2 | 5/2016 | Hirschman et al. |
| 2002/0128594 | A1 | 9/2002 | Das et al. |
| 2002/0129471 | A1 | 9/2002 | Wang |
| 2003/0014035 | A1 | 1/2003 | Trombley, III et al. |
| 2003/0139640 | A1 | 7/2003 | Whittacre et al. |
| 2003/0194894 | A1 | 10/2003 | Wariar et al. |
| 2003/0216609 | A1 | 11/2003 | Dell et al. |
| 2004/0054319 | A1 | 3/2004 | Langley et al. |
| 2004/0104160 | A1 | 6/2004 | Scagliarini et al. |
| 2004/0260143 | A1 | 12/2004 | Reilly et al. |
| 2005/0029465 | A1 | 2/2005 | Lemer |
| 2005/0085682 | A1 | 4/2005 | Sasaki et al. |
| 2005/0107698 | A1 | 5/2005 | Powers et al. |
| 2005/0187515 | A1 | 8/2005 | Varrichio et al. |
| 2005/0277833 | A1 | 12/2005 | Williams |
| 2005/0278066 | A1 | 12/2005 | Graves et al. |
| 2006/0015056 | A1 | 1/2006 | Ellingboe et al. |
| 2006/0151048 | A1 | 7/2006 | Tochon-Danguy et al. |
| 2006/0164093 | A1 | 7/2006 | Ooe et al. |
| 2006/0173419 | A1 | 8/2006 | Malcolm |
| 2006/0235353 | A1 | 10/2006 | Gelfand et al. |
| 2007/0080223 | A1 | 4/2007 | Japuntich |
| 2007/0140958 | A1 | 6/2007 | deKemp |

(56)                References Cited

U.S. PATENT DOCUMENTS

| | | |
|---|---|---|
| 2007/0213848 A1 | 9/2007 | deKemp et al. |
| 2007/0226175 A1 | 9/2007 | Resnic et al. |
| 2007/0232980 A1 | 10/2007 | Felt et al. |
| 2007/0260213 A1 | 11/2007 | Williams et al. |
| 2007/0282263 A1 | 12/2007 | Kalafut et al. |
| 2008/0015794 A1 | 1/2008 | Eiler et al. |
| 2008/0035542 A1 | 2/2008 | Mourtada et al. |
| 2008/0071219 A1 | 3/2008 | Rhinehart et al. |
| 2008/0093564 A1 | 4/2008 | Tartaglia et al. |
| 2008/0128626 A1 | 6/2008 | Rousso et al. |
| 2008/0131362 A1 | 6/2008 | Rousso et al. |
| 2008/0152083 A1 | 6/2008 | Juni |
| 2008/0166292 A1 | 7/2008 | Levin et al. |
| 2008/0177126 A1 | 7/2008 | Tate et al. |
| 2008/0191148 A1 | 8/2008 | Gibson |
| 2008/0195249 A1 | 8/2008 | Rousso et al. |
| 2008/0200747 A1 | 8/2008 | Wagner et al. |
| 2008/0203318 A1 | 8/2008 | Wagner et al. |
| 2008/0224065 A1 | 9/2008 | Pollard Jr. |
| 2008/0237502 A1 | 10/2008 | Fago |
| 2008/0242915 A1 | 10/2008 | Jackson et al. |
| 2008/0260580 A1 | 10/2008 | Helle et al. |
| 2009/0032729 A1 | 2/2009 | Piancastelli |
| 2009/0112478 A1 | 4/2009 | Mueller, Jr. et al. |
| 2009/0155167 A1 | 6/2009 | Powell et al. |
| 2009/0224171 A1 | 9/2009 | Verbokkem |
| 2009/0312630 A1 | 12/2009 | Hidem et al. |
| 2009/0312635 A1 | 12/2009 | Shimchuk et al. |
| 2010/0030009 A1 | 2/2010 | Lemer |
| 2010/0312039 A1 | 12/2010 | Quirico et al. |
| 2011/0071392 A1 | 3/2011 | Quirico et al. |
| 2011/0172524 A1 | 7/2011 | Hidem et al. |
| 2011/0178359 A1 | 7/2011 | Hirschman et al. |
| 2011/0209764 A1 | 9/2011 | Uber et al. |
| 2012/0098671 A1 | 4/2012 | Wieczorek et al. |
| 2012/0305730 A1 | 12/2012 | Balestracci |
| 2012/0310031 A1 | 12/2012 | Quirico et al. |
| 2012/0312980 A1 | 12/2012 | Whitehouse |
| 2013/0300109 A1 | 11/2013 | Balestracci et al. |
| 2014/0084187 A1 | 3/2014 | Quirico et al. |
| 2014/0175959 A1 | 6/2014 | Quirico et al. |
| 2014/0343418 A1 | 11/2014 | Quirico et al. |
| 2014/0374614 A1 | 12/2014 | Hidem et al. |
| 2014/0374615 A1 | 12/2014 | Hidem et al. |
| 2015/0260855 A1 | 9/2015 | McQuaid et al. |
| 2023/0093338 A1* | 3/2023 | Nandi .................... G16H 40/67 600/5 |
| 2024/0013946 A1* | 1/2024 | Lefort .................. G21G 1/0005 |
| 2024/0076248 A1* | 3/2024 | Vergote ................. C07B 59/008 |

FOREIGN PATENT DOCUMENTS

| | | |
|---|---|---|
| CN | 1137239 A | 12/1996 |
| CN | 1431488 A | 7/2003 |
| CN | 1460849 A | 12/2003 |
| CN | 1471644 A | 1/2004 |
| CN | 2677923 Y | 2/2005 |
| CN | 1946432 A | 4/2007 |
| CN | 1968653 A | 5/2007 |
| CN | 101015459 A | 8/2007 |
| CN | 201017036 Y | 2/2008 |
| CN | 101401009 A | 4/2009 |
| CN | 101801440 A | 8/2010 |
| CN | 104332198 A | 2/2015 |
| CN | 104536031 A | 4/2015 |
| CN | 104597472 A | 5/2015 |
| DE | 19622184 A1 | 12/1997 |
| DE | 19918342 B4 | 5/2017 |
| EP | 102121 A1 | 3/1984 |
| EP | 117752 A2 | 9/1984 |
| EP | 160303 A2 | 11/1985 |
| EP | 310148 A2 | 4/1989 |
| EP | 317114 A1 | 5/1989 |
| EP | 319148 A2 | 6/1989 |

| | | |
|---|---|---|
| EP | 919249 A1 | 6/1999 |
| EP | 1421960 A1 | 5/2004 |
| EP | 1772157 A1 | 4/2007 |
| EP | 1820730 A1 | 8/2007 |
| EP | 2332593 A2 | 6/2011 |
| EP | 2011126 B1 | 5/2012 |
| EP | 2492920 A2 | 8/2012 |
| EP | 2542276 A1 | 1/2013 |
| EP | 2896049 A1 | 7/2015 |
| FR | 2867084 A1 | 9/2005 |
| JP | 2000350783 A | 12/2000 |
| JP | 3137622 B1 | 2/2001 |
| JP | 2003520780 A | 7/2003 |
| JP | 2006017660 A | 1/2006 |
| JP | 2006043212 A | 2/2006 |
| JP | 2006325826 A | 12/2006 |
| JP | 2008023346 A | 2/2008 |
| JP | 2011161262 A | 8/2011 |
| KR | 960003726 B1 | 3/1996 |
| KR | 20150125046 A | 11/2015 |
| NO | 2007016173 A1 | 2/2007 |
| RU | 2131273 C1 | 6/1999 |
| RU | 2288755 C1 | 12/2006 |
| RU | 65383 U1 | 8/2007 |
| RU | 2429886 C2 | 9/2011 |
| RU | 2575309 C2 | 2/2016 |
| RU | 2599866 C2 | 10/2016 |
| RU | 2606169 C2 | 1/2017 |
| SU | 244513 A1 | 12/1969 |
| TW | 391868 B | 6/2000 |
| WO | 9615337 A1 | 5/1996 |
| WO | 9956117 A1 | 11/1999 |
| WO | 0156634 A1 | 8/2001 |
| WO | 02096335 A2 | 12/2002 |
| WO | 03034444 A1 | 4/2003 |
| WO | 2004004787 A2 | 1/2004 |
| WO | 2004059661 A1 | 7/2004 |
| WO | 2004080523 A2 | 9/2004 |
| WO | 2005002971 A1 | 1/2005 |
| WO | 2006007750 A1 | 1/2006 |
| WO | 2006026603 A2 | 3/2006 |
| WO | 2006074473 A2 | 7/2006 |
| WO | 2006129301 A2 | 12/2006 |
| WO | 2006135374 A2 | 12/2006 |
| WO | 2007016170 A1 | 2/2007 |
| WO | 2007030249 A2 | 3/2007 |
| WO | 2007041017 A1 | 4/2007 |
| WO | 2007071022 A1 | 6/2007 |
| WO | 2007082093 A2 | 7/2007 |
| WO | 2007096119 A2 | 8/2007 |
| WO | 2007104133 A1 | 9/2007 |
| WO | 2007149108 A2 | 12/2007 |
| WO | 2008028165 A2 | 3/2008 |
| WO | 2008037939 A2 | 4/2008 |
| WO | 2008066586 A2 | 6/2008 |
| WO | 2008082966 A2 | 7/2008 |
| WO | 2008140351 A1 | 11/2008 |
| WO | 2009152320 A2 | 12/2009 |
| WO | 2009152323 A2 | 12/2009 |
| WO | 2010020596 A1 | 2/2010 |
| WO | 2011126522 A2 | 10/2011 |
| WO | 2013082699 A1 | 6/2013 |
| WO | 2013085428 A1 | 6/2013 |
| WO | 2014036627 A1 | 3/2014 |
| WO | 2018057634 A1 | 3/2018 |
| WO | 2018057635 A1 | 3/2018 |
| WO | 2018057636 A1 | 3/2018 |
| WO | 2019191384 A1 | 10/2019 |
| WO | 2019191386 A1 | 10/2019 |

OTHER PUBLICATIONS 337-1110_662795: Staff's Response to Respondents' Motion for Summary Determination of Noninfringement of U.S. Pat. No. 9,750,869; U.S. Pat. No. 9,750,870; and U.S. Pat. No. 9,814,826 by Respondents' Version 3.1 and 4 Designs (Motion Response/ Reply); 1-1389338: "Staff's Response to Respondents' Motion for Summary Determination of Noninfringement of U.S. Pat. No. 9,750,869;

(56) References Cited

OTHER PUBLICATIONS

U.S. Pat. No. 9,750,870; and U.S. Pat. No. 9,814,826 by Respondents' Version 3.1 and 4 Designs", create date Nov. 28, 2018, www.edis.usitc.gov.
337-1110_662796: Staff's Response to Complainant's Motion for Summary Determination of Infringement and Satisfaction of the Economic & Technical Prongs of the Domestic Industry Requirement (Motion Response/Reply); 1-1389340: "Staff's Response to Complainant's Motion for Summary Determination of Infringement & Satisfaction of the Economic & Technical Prongs of the Domestic Industry Requirement", create date Nov. 28, 2018, www.edis.usitc. gov.
Attachment D: Respondents' Obviousness Contentions, Exchanged in ITC Investigation No. 337-TA-1110, Aug. 8, 2018, 38 pages. (Confidential Business Information Redacted).
Exhibit D.1: U.S. Pat. No. 9,814,826 Claim Chart—Obviousness Over Klein, Exchanged in ITC Investigation No. 337-TA-1110, Aug. 8, 2018, 207 pages. (Confidential Business Information Redacted).
Exhibit D.2: U.S. Pat. No. 9,750,869 Claim Chart—Obviousness Over Klein, Exchanged in ITC Investigation No. 337-TA-1110, Aug. 8, 2018, 244 pages. (Confidential Business Information Redacted).
Exhibit D.3: U.S. Pat. No. 9,750,870 Claim Chart—Obviousness Over Klein, Exchanged in ITC Investigation No. 337-TA-1110, Aug. 8, 2018, 172 pages. (Confidential Business Information Redacted).
Exhibit D.4: U.S. Pat. No. 9,814,826 Claim Chart—Obviousness Over Cardiogen-82, Exchanged in ITC Investigation No. 337-TA-1110, Aug. 8, 2018, 224 pages. (Confidential Business Information Redacted).
Exhibit D.5: U.S. Pat. No. 9,750,869 Claim Chart—Obviousness Over Cardiogen-82, Exchanged in ITC Investigation No. 337-TA-1110, Aug. 8, 2018, 255 pages. (Confidential Business Information Redacted).
Exhibit D.6: U.S. Pat. No. 9,750,870 Claim Chart—Obviousness Over Cardiogen-82, Exchanged in ITC Investigation No. 337-TA-1110, Aug. 8, 2018, 199 pages. (Confidential Business Information Redacted).
Bracco Diagnostics Inc.'s Rebuttal Contentions in Response to Respondents' Aug. 8, 2018 Contentions (Including Responses to OUII Staff ROG Nos. 13, 18, 19, 20-22, 32 and Respondents' ROG Nos. 5, 9-11, 18, 33), Investigation No. 337-TA-1110, Aug. 15, 2018, 35 pages. (Confidential Business Information Redacted).
Supplemental Exhibit 1, Response to Supplemental Exhibit D.1: U.S. Pat. No. 9,814,826 Invalidity Contentions, Exchanged in ITC Investigation No. 337-TA-1110, Aug. 15, 2018, 22 pages. (Confidential Business Information Redacted).
Supplemental Exhibit 2, Response to Supplemental Exhibit D.2: U.S. Pat. No. 9,750,869 Invalidity Contentions, Exchanged in ITC Investigation No. 337-TA-1110, Aug. 15, 2018, 23 pages. (Confidential Business Information Redacted).
Supplemental Exhibit 3, Complainant's Supplemental Response to Respondents' Supplemental Exhibit D.3: U.S. Pat. No. 9,750,870 Invalidity Contentions, Exchanged in ITC Investigation No. 337-TA-1110, Aug. 15, 2018, 19 pages. (Confidential Business Information Redacted).
Bracco Diagnostics Inc.'s Supplemental Rebuttal Contentions in Response to Respondents' Aug. 8, 2018 Contentions Pursuant to Order No. 16, Investigation No. 337-TA-1110, Aug. 23, 2018, 18 pages. (Confidential Business Information Redacted).
Supplemental Exhibit 1, Response to Supplemental Exhibit D.1: U.S. Pat. No. 9,814,826 Invalidity Contentions, Exchanged in ITC Investigation No. 337-TA-1110, Aug. 23, 2018, 22 pages. (Confidential Business Information Redacted).
Supplemental Exhibit 2, Response to Supplemental Exhibit D.2: U.S. Pat. No. 9,750,869 Invalidity Contentions, Exchanged in ITC Investigation No. 337-TA-1110, Aug. 23, 2018, 25 pages. (Confidential Business Information Redacted).
Supplemental Exhibit 3, Complainant's Supplemental Response to Respondents' Supplemental Exhibit D.3: U.S. Pat. No. 9,750,870 Invalidity Contentions, Aug. 23, 2018, 26 pages. (Confidential Business Information Redacted).

Exhibit 4, Response to Exhibit D.4: U.S. Pat. No. 9,814,826 Invalidity Contentions, Aug. 23, 2018, 37 pages. (Confidential Business Information Redacted).
Exhibit 5, Response to Exhibit D.5: U.S. Pat. No. 9,814,826 Invalidity Contentions, Aug. 23, 2018, 39 pages. (Confidential Business Information Redacted).
Supplemental Exhibit 6, Complainant's Supplemental Response to Respondents' Supplemental Exhibit D.6: U.S. Pat. No. 9,750,870 Invalidity Contentions, Aug. 23, 2018, 44 pages. (Confidential Business Information Redacted).
337-1110_652068: Respondents' Jubilant DraxImage Inc., Jubilant Pharma Limited, and Jubilant Life Sciences Limited Notice of Prior Art (Notice of Prior Art); 1-1311880: "Respondents First Supplemental Notice of Prior Art", create date Aug. 3, 2018, www.edis. usitc.gov, 29 pages.
Respondents' Pre-Hearing Brief, Public Version, Investigation No. 337-TA-1110, Dec. 12, 2018, 550 pages.
Complainant Bracco Diagnostics Inc.'s Pre-Hearing Brief, Public Version, Inv. No. 337-TA-1110, Dec. 13, 2018, 568 pages.
Report of Robert T. Stone, Ph.D on Invalidity of U.S. Pat. No. 9,750,869, U.S. Pat. No. 9,750,870 and U.S. Pat. No. 9,814,826, Sep. 17, 2018, 1051 pages. (Confidential Business Information Redacted).
Corrected Expert Report of Norbert J. Pelc, Sc.D, Investigation No. 337-TA-1110, Oct. 1, 2018, 289 pages. (Confidential Business Information Redacted).
Declaration of Robert T. Stone, Ph.D., *Jubilant DraxImage Inc. v. Bracco Diagnostics Inc.,* IPR2018-01448 and IPR2018-01450, Exhibit 1015, Aug. 17, 2018, 267 pages.
Curriculum Vitae of Robert T. Stone, Ph.D., *Jubilant DraxImage Inc. v. Bracco Diagnostics Inc.,* IPR2018-01448, Exhibit 1016, filed Aug. 22, 2018, 10 pages.
Declaration of Venkatesh L. Murthy, M.D., Ph.D., *Jubilant DraxImage Inc. v. Bracco Diagnostics Inc.,* IPR2018-01448, Exhibit 1017, Aug. 14, 2018, 52 pages.
US Pharmacopeia 23 National Formulary 18, 1995, 5 pages (cited as Exhibit 1019 in IPR2018-01448, *Jubilant DraxImage Inc. v. Bracco Diagnostics Inc.*).
Declaration of Andy Adler, Ph.D., *Jubilant DraxImage Inc. v. Bracco Diagnostics Inc.,* IPR2018-01448, Exhibit 1020, Aug. 17, 2018, 156 pages.
Bracco CardioGen-82 Infusion System User's Guide, Rev. 07, Jul. 20, 2004, 49 pages (cited as Exhibit 1021 in IPR2018-01448, *Jubilant DraxImage Inc. v. Bracco Diagnostics Inc.*).
Chatal et al., "Story of rubidium-82 and advantages for myocardial perfusion PET imaging," Frontiers in Medicine, v. 2, art. 65, Sep. 11, 2015, pp. 1-7 (cited as Exhibit 1026 in IPR2018-01448, *Jubilant DraxImage Inc. v. Bracco Diagnostics Inc.*).
ISO 13485:2003—Medical Devices—Quality Management Systems—Requirements for Regulatory Purposes, Jul. 15, 2003, 64 pages (cited as Exhibit 1028 in IPR2018-01448, *Jubilant DraxImage Inc. v. Bracco Diagnostics Inc.*).
21 CFR Part 820.1, US Food and Drug Administration, HHS, 2005, pp. 152-153 (cited as Exhibit 1029 in IPR2018-01448, *Jubilant DraxImage Inc. v. Bracco Diagnostics Inc.*).
EN 62274:2005—Medical Electrical Equipment—Safety of Radiotherapy Record and Verify Systems, Dec. 28, 2005, 22 pages (cited as Exhibit 1030 in IPR2018-01448, *Jubilant DraxImage Inc. v. Bracco Diagnostics Inc.*).
21 CFR Part 11.1, US Food and Drug Administration, HHS, 2004, pp. 109-110 (cited as Exhibit 1031 in IPR2018-01448, *Jubilant DraxImage Inc. v. Bracco Diagnostics Inc.*).
10 CFR Part 20.1001-1002, Nuclear Regulatory Commission, 2005, pp. 317-318 (cited as Exhibit 1032 in IPR2018-01448, *Jubilant DraxImage Inc. v. Bracco Diagnostics Inc.*).
10 CFR Part 20.1003, Nuclear Regulatory Commission, 2005, pp. 318-324 (cited as Exhibit 1033 in IPR2018-01448, *Jubilant DraxImage Inc. v. Bracco Diagnostics Inc.*).
Wang et al., Handbook of Radioactive Nuclides, The Chemical Rubber Co., 1969, 59 pages (cited as Exhibit 1034 in IPR2018-01448, *Jubilant DraxImage Inc. v. Bracco Diagnostics Inc.*).
Bates et al., "Effect of Computerized Physician Order Entry and a Team Intervention on Prevention of Serious Medication Errors,"

(56) References Cited

OTHER PUBLICATIONS

JAMA, vol. 280, No. 15, Oct. 21, 1998, pp. 1311-1316 (cited as Exhibit 1035 in IPR2018-01448, *Jubilant DraxImage Inc.* v. *Bracco Diagnostics Inc.*).
Bates et al., "The Impact of Computerized Physician Order Entry on Medication Error Prevention," Journal of the American Medical Informatics Association, vol. 6, No. 4, Jul./Aug. 1999, pp. 313-321 (cited as Exhibit 1036 in IPR2018-01448, *Jubilant DraxImage Inc.* v. *Bracco Diagnostics Inc.*).
Medical Devices Security Technical Implementation Guide, Defense Information Systems Agency, Version 1, Release 1, Jul. 27, 2010, 56 pages (cited as Exhibit 1037 in IPR2018-01448, *Jubilant DraxImage Inc.* v. *Bracco Diagnostics Inc.*).
Implementation Guide for the Use of Bar Code Technology in Healthcare, HIMSS, 2003, 72 pages (cited as Exhibit 1038 in IPR2018-01448, *Jubilant DraxImage Inc.* v. *Bracco Diagnostics Inc.*).
337-TA-1110: Complainant Bracco Diagnostics Inc.'s Responses to Respondents Jubilant DraxImage, Inc.'s, Jubilant Pharma Limited's, and Jubilant Life Sciences' Fourth Set of Interrogatories (No. 68), Aug. 6, 2018, 11 pages (cited as Exhibit 1039 in IPR2018-01448, *Jubilant DraxImage Inc.* v. *Bracco Diagnostics Inc.*).
Declaration of Carol Wadke, *Jubilant DraxImage Inc.* v. *Bracco Diagnostics Inc.*, IPR2018-01448, Exhibit 1042, Jul. 27, 2018, 174 pages.
Petition for Inter Partes Review of U.S. Pat. No. 9,299,468, *Jubilant DraxImage Inc.* v. *Bracco Diagnostics Inc.*, IPR2018-01448, Aug. 22, 2018, 97 pages.
Patent Owner's Submission of Mandatory Notice Information Under 37 CFR 42.8(a)(2), *Jubilant DraxImage Inc.* v. *Bracco Diagnostics Inc.*, IPR2018-01448, Sep. 13, 2018, 4 pages.
Patent Owner's Preliminary Response, *Jubilant DraxImage Inc.* v. *Bracco Diagnostics Inc.*, IPR2018-01448, Nov. 29, 2018, 79 pages.
Redline comparison between US Patent Publication No. 2004/0260143 A1 (Reilly et al.), published 2004-12-23 and U.S. Pat. No. 6,767,319 B2 (Reilly et al.), issued Jul. 27, 2004, filed Nov. 29, 2018 as Exhibit 2002 in IPR2018-01448, *Jubilant DraxImage Inc.* v. *Bracco Diagnostics Inc.*, 22 pages.
"Alaris GH Syringe Pump Directions For Use," Cardinal Health, Oct. 2005, 34 pages.
Alvarez-Diez et al. "Manufacture of strontium-82/rubidium-82 generators and quality control of rubidium-82 chloride for myocardial perfusion imaging in patients using positron emission tomography," Applied Radiation and Isotopes, 1999, pp. 1015-1023.
"Auto Syringe AS40A: Model AS40A Infusion Pump Operation Manual," Baxter, Aug. 1993, 84 pages.
"BodyGuard 323 Infusion Pump System Operator Manual," Caesarea Medical Electronics Ltd, Mar. 2009, 81 pages.
Brochure, "IV and Liquid Filters: Speedflow Adult 0.2 um Positive", http://www.gvs.it/flex/FixedPages/UK/LiquidFilters.php/L/UK/ID/Speedflow%20Adjust% . . . Retrieved from URL on Nov. 11, 2008.
BRACCO Brochure, "Rubidium 82 Infusion System, Easy to Operate . . . Automated . . . Complete", © Bracco Diagnostics, Inc., 0605-002NA, Jun. 2001, (2 pages).
"CardioGen-82 Infusion System User's Guide," Medical Product Service GmbH, Jul. 3, 2007, 53 pages.
"CardioGen-82 Rubidium Rb 82 Generator For Elution of Rubidium Chloride Rb 82 Injection," Bracco Diagnostics, May 2000, 13 pages.
Daraban et al., "Efficiency Calibration in Gamma Spectrometry by Using 232Th Series Radionuclides," Romanian Journal of Physics, vol. 58, Supplement, 2013, pp. S99-S107.
Neil J. Epstein, "A Rb82 infusion system for quantitative perfusion imaging with 3D PET" Applied Radiation and Isotopes, vol. 60, Feb. 9, 2004, pp. 921-927, XP002557544 DOI:10, 1016/j. apradiso. 2004.02.002.
International Patent Application No. PCT/US2021/018807, International Search Report and Written Opinion mailed Apr. 20, 2021, 13 pages.

Imaging Technology News, web exclusive: "FDG-PET Injector Thrusts New Life into Molecular Imaging", Apr. 2008, 2 pages.
R. Klein, "Precise 82RB infusion system for cardiac perfusion measurement using 3D positron emission tomography", Ottawa-Carleton Institute for Electrical and Computer Engineering School of Information Technology and Engineering (Electrical & Computer Engineering), Feb. 2005, 147 pages.
R. Klein, "Precision control of eluted Activity from a Sr/Rb generator for cardiac positron emission tomography", Proceedings of the 26th Annual International Conference of the IEEE EMBS San Francisco, CA, USA, Sep. 1-5, 2004, 4 pages.
R. Klein, "Precision controlled elution of a Sr82/Rb82 generator for cardiac perfusion imaging with positron emission tomography" Physics in Medicine and Biology, vol. 52, Jan. 11, 2007, pp. 659-673, XP002557545 DOI:10,1088/0031-9155/52/3/009.
Kost, "Preventing Medical Errors in Point-of-Care Testing," Archives of Pathology & Laboratory Medicine, vol. 125, No. 10, Oct. 2001, pp. 1307-1315.
Lemer Pax, Posijet® Integrated FDG dispensing and infusion system, www.lemerpax.com (copyright date May 2008).
Leveson, "Medical Devices: The Therac-25*," Appendix of: Safeware: System Safety and Computers, 1995, 49 pages.
Lortie et al., "Quantification of myocardial blood flow with 82Rb dynamic PET imaging," Eur. J. Nucl. Med. Mol. Imaging, vol. 34, 2007, pp. 1765-1774.
Luca et al., "Calibration of the High and Low Resolution Gamma-Ray Spectrometers," Romanian Reports in Physics, vol. 64, No. 4, 2012, pp. 968-976.
Machine translation of abstract of RU2307378 published Sep. 27, 2007 (Oao Sojuztsvetmetavtomatika).
"Medfusion 3000 Series Technical Service Manual," Smiths Medical, 2010, 184 pages.
Neirincks et al., "Evaluation of Inorganic Adsorbents for the Rubidium-82 Generator: I. Hydrous SnO2," The Journal of Nuclear Medicine, vol. 23, No. 3, Jan. 1, 1982, pp. 245-249.
Rawool-Sullivan et al., "Use of Wavelet Denoising in Identifying Radioactive Isotopes Using a Gamma-Ray Spectrum," Summary #2826 American Nuclear Society, Winter 2010 conference, Nov. 1, 2010, 4 pages.
337-1110_640015: Public Version of Complaint and Exhibits 1-28 (Complaint); 1-1283977: "640015 Public Complaint: GreenbergTraurig's letter dated Mar. 27, 2018 re Complainant's filing of documents to support Bracco's request that the Commission commence 337 investigation", create date Apr. 13, 2018, www.edis.usitc.gov.
337-1110_643191: Notice of Institution of Investigation (Notice); 1-1285952: "1285952: Notice of Institution of Investigation Inv. No. 337-TA-1110", create date Apr. 25, 2018, www.edis.usitc.gov.
337-1110_647318: Joint List of Disputed and Undisputed Claim Terms (Other); 1-1298795: "1298795: Joint List of Disputed and Undisputed Claim Terms", create date Jun. 8, 2018, www.edis.usitc. gov.
337-1110_648102: Proposed Construction of Disputed Claim Terms (Response/Submission to ALJ Order); 1-1301950: "Proposed Constructions", create date Jun. 18, 2018, www.edis.usitc.gov.
337-1110_650007: Respondent Jubilant DraxImage Inc., Jubilant Pharma Limited, and Jubilant Life Sciences Limited's Notice of Prior Art (Notice of Prior Art); 1-1306444: "Notice of Prior Art", create date Jul. 10, 2018, www.edis.usitc.gov.
337-1110_652080: Joint Unopposed Motion for Leave to File Joint Submission of Identification of Claim Terms and Proposed Constructions Thereof out of Time (Motion); 2-1311910: "Identification of Claim Terms", create date Aug. 3, 2018, www.edis.usitc.gov. create date Aug. 3, 2018, www.edis.usitc.gov.
337-1110_652479: Granting Joint Motion to File Identification of Claim Terms and Constructions out of Time (Order); 1-1313857: "652479: Order No. 14", create date Aug. 8, 2018, www.edis.usitc. gov.
337-1110_661785: Complainant Bracco Diagnostics Inc.'s Motion for Summary Determination of Infringement and Satisfaction of the Economic and Technical Prongs of the Domestic Industry Requirement (Motion); 1-1385894: "Letter to Barton", create date Nov. 14, 2018, www.edis.usitc.gov.

(56)                   References Cited

OTHER PUBLICATIONS 337-1110_661785: Complainant Bracco Diagnostics Inc.'s Motion for Summary Determination of Infringement and Satisfaction of the Economic and Technical Prongs of the Domestic Industry Requirement (Motion); 2-1385895: "Motion for Summary Determination", create date Nov. 14, 2018, www.edis.usitc.gov.
337-1110_661785: Complainant Bracco Diagnostics Inc.'s Motion for Summary Determination of Infringement and Satisfaction of the Economic and Technical Prongs of the Domestic Industry Requirement (Motion); 3-1385896: "Chart of Undisputed Material Facts", create date Nov. 14, 2018, www.edis.usitc.gov.
337-1110_661851: Errata to Staff's Response to Complainant's Motion for Summary Determination of Infringement and Satisfaction of the Economic and Technical Prongs of the Domestic Industry Requirement (Motion Response/Reply); 1-1385993:, create date Nov. 14, 2018, www.edis.usitc.gov.
337-1110_660985: Respondents' Motion for Summary Determination of Noninfringement of U.S. Pat. No. 9,750,869, U.S. Pat. No. 9,750,870, and U.S. Pat. No. 9,814,826 by Respondents' Version 3.1 and Version 4 Designs (Motion); 1-1383714: "Respondents' Motion for Summary Determination (PV)", create date Nov. 5, 2018, www.edis.usitc.gov.
337-1110_660985: Respondents' Motion for Summary Determination of Noninfringement of U.S. Pat. No. 9,750,869, U.S. Pat. No. 9,750,870, and U.S. Pat. No. 9,814,826 by Respondents' Version 3.1 and Version 4 Designs (Motion); 2-1383715: "Memorandum in Support of Respondents' Motion for Summary Determination (PV)", create date Nov. 5, 2018, www.edis.usitc.gov.
337-1110_660985: Respondents' Motion for Summary Determination of Noninfringement of U.S. Pat. No. 9,750,869, U.S. Pat. No. 9,750,870, and U.S. Pat. No. 9,814,826 by Respondents' Version 3.1 and Version 4 Designs (Motion); 17-1383730: "Chart of Material Facts in Support of Respondents' MSD", create date Nov. 5, 2018, www.edis.usitc.gov.
337-1110_661010: Complainant Bracco Diagnostics Inc.'s Motion for Summary Determination of Infringement and Satisfaction of the Economic and Technical Prongs of the Domestic Industry Requirement (Motion); 1-1383879: "Bracco's Motion for Summary Determination", create date Nov. 5, 2018, www.edis.usitc.gov.
337-1110_661010: Complainant Bracco Diagnostics Inc.'s Motion for Summary Determination of Infringement and Satisfaction of the Economic and Technical Prongs of the Domestic Industry Requirement (Motion); 2-1383880: "Bracco's Chart of Undisputed Material Facts", create date Nov. 5, 2018, www.edis.usitc.gov.
337-1110_661038: Respondents' Unopposed Motion to Replace Respondents' Chart of Material Facts in Support of Motion for Summary Determination (Motion); 1-1383923: "Respondents' Unopposed Motion to Replace Respondents' Chart of Material Facts in Support of Motion for Summary Determination (Public Version)", create date Nov. 5, 2018, www.edis.usitc.gov.
337-1110_662007: Respondents' Memorandum in Opposition of Complainant's Motion for Summary Determination of Infringement and Satisfaction of the Economic and Technical Prongs of the Domestic Industry Requirement (Motion Response/Reply); 1-1386474: "Respondents' Memorandum in Opposition to Complainant's Motion for Summary Determination (PV)", create date Nov. 16, 2018, www.edis.usitc.gov.
Ruby Rubidium Elution System User Manual, Jubilant DraxImage, Version 7, Created Jun. 3, 2014, Modified Jan. 9, 2015, 58 pages.
Intego PET Infusion System Operation Manual, Medrad, Rev. G, Jun. 2013, 142 pages.
Commission Investigative Staff's Prehearing Brief, Inv. No. 337-TA-1110, Dec. 20, 2018, 129 pages. (Confidential Business Information Redacted).

Saha et al., "Use of the 82Sr/82Rb Generator in Clinical PET Studies*," International Journal of Radiation Applications and Instrumentation, Part B. Nuclear Medicine and Biology, vol. 17, No. 8, 1990, pp. 763-768.
Yano et al., "Evaluation and Application of Alumina-Based Rb-82 Generators Charged with High Levels of Sr-82/85," The Journal of Nuclear Medicine, vol. 20, No. 9, 1979, pp. 961-966.
Yano et al., "A Precision Flow-Controlled Rb-82 Generator for Bolus or Constant-Infusion Studies of the Heart and Brain," The Journal of Nuclear Medicine, Preliminary Notes, vol. 22, No. 11, 1981, pp. 1006-1010.
Yano, "Essentials of a Rubidium-82 Generator for Nuclear Medicine," International Journal of Radiation Applications and Instrumentation, Part A. Applied Radiation and Isotopes, vol. 38, No. 3, 1987, pp. 205-211.
337-1110_ 662084: Complainant Bracco Diagnostics Inc.'s Response to Jubilant's Motion for Summary Determination pf Noninfringement of U.S. Pat. No. 9,750,869, U.S. Pat. No. 9,750,870, and U.S. Pat. No. 9,814,826 by Jubilant's Version 3.1 and Version 4 Designs and Memorandum in Support Thereof (Motion Response/Reply); 1-1386969: "Complainant's Response to Motion for Summary Determination", create date Nov. 19, 2018, www.edis.usitc.gov.
Declaration of Robert T. Stone, Ph.D., *Jubilant DraxImage Inc. v. Bracco Diagnostics Inc.*, IPR2018-01449, Exhibit 1015, Aug. 16, 2018, 175 pages.
Petition for Inter Partes Review of U.S. Pat. No. 9,299,467, *Jubilant DraxImage Inc. v. Bracco Diagnostics Inc.*, PR2018-01449, Aug. 22, 2018, 77 pages.
Patent Owner's Submission of Mandatory Notice Information Under 37 CFR 42.8(a)(2), *Jubilant DraxImage Inc. v. Bracco Diagnostics Inc.*, IPR2018-01449, Sep. 13, 2018, 4 pages.
Patent Owner's Preliminary Response, *Jubilant DraxImage Inc. v. Bracco Diagnostics Inc.*, IPR2018-01449, Nov. 29, 2018, 75 pages.
Petition for Inter Partes Review of U.S. Pat. No. 9,299,468, *Jubilant DraxImage Inc. v. Bracco Diagnostics Inc.*, IPR2018-01450, Aug. 22, 2018, 56 pages.
Patent Owner's Submission of Mandatory Notice Information Under 37 CFR 42.8(a)(2), *Jubilant DraxImage Inc. v. Bracco Diagnostics Inc.*, IPR2018-01450, Sep. 13, 2018, 4 pages.
Patent Owner's Preliminary Response, *Jubilant DraxImage Inc. v. Bracco Diagnostics Inc.*, IPR2018-01450, Nov. 30, 2018, 64 pages.
Decision to Institute in IPR2018-01448, U.S. Pat. No. 9,299,468 B2, *Jubilant DraxImage Inc. v. Bracco Diagnostics Inc.*, Feb. 8, 2019, 22 pages.
Decision to Institute in IPR2018-01449, U.S. Pat. No. 9,299,467 B2, *Jubilant DraxImage Inc. v. Bracco Diagnostics Inc.*, Feb. 8, 2019, 21 pages.
Decision to Institute in IPR2018-01450, U.S. Pat. No. 9,299,468 B2, *Jubilant DraxImage Inc. v. Bracco Diagnostics Inc.*, Feb. 8, 2019, 19 pages.
ELFO Automatic Radiopharmaceutical Injection System for PET Imaging, Date Not Identified, 3 pages.
Commission Opinion, Inv. No. 337-TA-1110, Public Version, Dec. 11, 2019, 43 pages.
Bracco Diagnostics Inc.'s Petition for Review with Exhibits 1, 2 and 3, Inv. No. 337-TA-1110, Dec. 23, 2019, 240 pages.
Initial Determination on Violation of Section 337 and Recommended Determination on Remedy and Bond, Inv. No. 337-TA-1110, Public Version, Aug. 1, 2019, 185 pages.
Final Written Decision in IPR2018-01448, U.S. Pat. No. 9,299,468 B2, *Jubilant DraxImage Inc. v. Bracco Diagnostics Inc.*, Feb. 6, 2020, 98 pages.
Final Written Decision in IPR2018-01449, U.S. Pat. No. 9,299,467 B2, *Jubilant DraxImage Inc. v. Bracco Diagnostics Inc.*, Feb. 6, 2020, 58 pages.
Final Written Decision in IPR2018-01450, U.S. Pat. No. 9,299,468 B2, *Jubilant DraxImage Inc. v. Bracco Diagnostics Inc.*, Feb. 6, 2020, 51 pages.

* cited by examiner

RADIOISOTOPE GENERATOR EARLY BREAKTHROUGH DETECTION

CROSS-REFERENCE

This application is a 35 U.S.C. 371 national phase filing from International Application No. PCT/US2021/018807, filed Feb. 19, 2021, which claims the benefit of U.S. Provisional Patent Application No. 62/979,886, filed Feb. 21, 2020. The entire contents of each application are incorporated herein by reference.

In addition, this application may be found related to U.S. Patent Publication No. 2020/0030522, filed Mar. 20, 2019 and titled "RADIOISOTOPE DELIVERY SYSTEM WITH MULTIPLE DETECTORS TO DETECT GAMMA AND BETA EMISSIONS," U.S. Patent Publication No. 2020/0016284, filed Mar. 20, 2019, now U.S. Pat. No. 10,751,432, issued Aug. 25, 2020 and titled "SHIELDING ASSEMBLY FOR A RADIOISOTOPE DELIVERY SYSTEM HAVING MULTIPLE RADIATION DETECTORS," and/or U.S. Patent Publication No. 2020/0030523, filed Mar. 20, 2019 and titled "SYSTEMS AND TECHNIQUES FOR GENERATING, INFUSING, AND CONTROLLING RADIOISOTOPE DELIVERY." The entire contents of each of these applications are incorporated herein by reference.

TECHNICAL FIELD

This disclosure relates to radiopharmaceuticals used in nuclear medicine and, more particularly, to systems and techniques for identifying and controlling parent radioisotope breakthrough from a radioisotope generator before the breakthrough occurs.

BACKGROUND

Nuclear medicine employs radioactive material for therapy and diagnostic imaging. Positron emission tomography (PET) is one type of diagnostic imaging, which utilizes doses of radiopharmaceutical. The doses of radiopharmaceutical may be injected or infused into a patient prior to or during a PET scan procedure. An infused dose of radiopharmaceutical can be absorbed by cells of a target organ of the patient and emit radiation. A PET scanner can detect the emitted radiation in order to generate image of an organ. For example, to image body tissue such as the myocardium, a patient may be injected or infused with rubidium-82 ($^{82}$Rb). Rubidium-82 may exhibit similar physiological uptake as potassium and, accordingly, may be taken into the myocardium following potassium pathways.

Rubidium-82 can be generated for nuclear medicine procedures using a strontium-rubidium generator ($^{82}$Sr/$^{82}$Rb generator). Rubidium-82 is a radioactive decay product of strontium-82. Typically, strontium-rubidium generators contain strontium bound to a generator column through which an eluant is flushed during operation. As strontium-82 decays to rubidium-82, the rubidium-82 may release from the generator column and enter the eluant. The resulting stream, which is called an eluate, can be injected or infused into a patient.

SUMMARY

In general, some embodiments of the present invention are directed to systems and techniques for predicting radioisotope generator breakthrough. For parent-daughter radioisotope systems, the radioisotope generator can contain the parent radioisotope bound on a generator column or other structure that decays to the daughter radioisotope, which is not necessarily isobaric, isotonic, isodiapheric, or isotopic to the parent radioisotope. The daughter radioisotope can be flushed from the radioisotope generator using an eluent, thereby generating a radioactive eluate for quality control analysis and/or injection into a patient for diagnostic imaging. Over time and repeated cycles of elution, the parent radioisotope in the radioisotope generator may itself release into the eluent during elution, e.g., at a level above that which is acceptable for introduction into a patient. This phenomenon, referred to as breakthrough, is desirably detected before the breakthrough occurs. With early detection, the radioisotope generator system and/or a manufacturer, operator, or other user of the radioisotope generator system may take interventional action to prevent the eluate with excessive level of parent radioisotope from being injected into a patient.

For example, a radioactive eluate containing a daughter radioisotope can be generated by passing the eluant across a substrate containing bound parent radioisotope. As the parent radioisotope decays into the daughter radioisotope, the daughter radioisotope may release from the substrate, causing the daughter radioisotope to release into the flowing eluant and thereby generating an eluate via elution. As the radioisotope generator approaches the end of its service life, the parent radioisotope may itself begin releasing from the substrate to which the parent radioisotope is bound, causing the parent radioisotope to release into the flowing eluate produced by the generator in addition to its decay product. The amount of parent radioisotope allowed to enter the eluate may be kept comparatively low. This is because the parent radioisotope may have a much longer half-life than the half-life of the daughter radioisotope and, if injected into the patient, will produce radioactive emissions inside of the patient for a longer period of time than the daughter. For example, in the case of a strontium-rubidium radioisotope generator, the parent strontium-82 radioisotope has a half-life of approximately 25.5 days whereas the half-life of the daughter rubidium-82 radioisotope is approximately 76 seconds, in addition to other different physical/chemical properties.

Operators of current radiopharmaceutical delivery systems can perform a periodic quality control check to determine if the eluate produced by the system has an undesired radioisotope above an acceptable level. The operator may generate a sample of eluate, transfer the sample to a dose calibrator, and then measure the activity of parent radioisotope (and/or other contaminant radioisotope) in the eluate. If the undesired radioisotope is above an acceptable level, the operate may take the radiopharmaceutical delivery system out of service until the radioisotope generator in the system can be refreshed and/or replaced with a new generator that produces eluate of acceptable quality. The unplanned removal of the radiopharmaceutical delivery system from service because of eluate quality control test results can have a number of operational impacts. For example, patient procedures scheduled using the radiopharmaceutical delivery system may need to be rescheduled or otherwise accommodated. Further, because an amount of time may need to pass between when the radiopharmaceutical delivery system is taken out of service and when the radioisotope generator can be replaced, the system may need to remain out of service for some time.

In accordance with some examples of the present disclosure, a radiopharmaceutical delivery system is described that can proactively and predicatively determine when breakthrough will likely occur. The system may measure the radioactivity of the radioactive eluate produced by the radioisotope generator, e.g., as a function of elution time and/or the volume of eluent passed through the radioisotope generator. This can provide a radioactivity profile, which may be referred to as a bolus curve in some implementations, for the radioactive eluate generated by the radioisotope generator during elution. The radioactivity profile can be analyzed to determine one or more characteristics of the profile indicative of breakthrough of the parent radioisotope into the radioactive eluate.

In practice, the shape of the radioactivity profile of the radioactive eluate generated by the radioisotope generator will change over time and/or successive elutions. One or more shape characteristics of the radioactivity profile that change from initial elution to elution when breakthrough occurs can be used to determine when breakthrough will occur, prior to breakthrough actually occurring. An example characteristics of the radioactivity profile that can be determined and compared to a threshold for the characteristic corresponding to breakthrough is a lapsed time and/or a lapse volume between a start of elution (e.g., a zero time or volume for the radioactivity profile) and a peak radioactivity. Since the peak radioactivity will shift over time and/or successive elutions—either to peak earlier in the elution or later in the elution, depending on the configuration and characteristics of the radioisotope generator system—the amount of time and/or volume that passes until the peak radioactivity is observed can be used as a characteristic indicative of breakthrough.

Characteristics of the radioactivity profile indicative of breakthrough are not limited to lapsed time or lapse volume from the start of elution to peak radioactivity. In general, the lapsed time and/or the lapsed volume between any two levels or points on the radioactivity profile can be used to provide a characteristic of the radioactivity profile indicative of breakthrough (e.g., provided the lapsed time and/or the lapsed volume between the two points changes from the first elution using the generator to a subsequent elution when breakthrough occurs). For example, a first predetermined level for determining the breakthrough characteristic may correspond to the start of elution or may be shifted to be measured at some time and/or volume of eluent pumped into the radioisotope generator occurring after the start of elution. Additionally, a second predetermined level for determining the breakthrough characteristic may correspond to the time and/or volume when peak radioactivity occurs or may be shifted to be measured at some time and/or volume of eluent pumped into the radioisotope generator occurring before or after peak radioactivity occurs.

To determine a characteristic of the radioactivity profile indicative of breakthrough, the radioactivity profile itself (e.g., the measured radioactivity of the eluate defining the profile) can be analyzed as a function of the cumulative time of elution and/or the cumulative volume of eluent pumped into the radioisotope generator. Additionally or alternatively, a derivative of the radioactivity profile can be analyzed, such as a first order derivative corresponding to a rate of change of the radioactivity profile, or a second order derivative corresponding to a rate of change of the first order derivative. Further additionally or alternatively, a derivative of the radioactivity profile higher than the second order can also be analyzed either alone or in combination with the radioactivity profile and/or derivatives thereof. Analyzing the derivative of the measured radioactivity defining the radioactivity profile instead of the measured radioactivity data itself may yield additional informational insights.

In one example, an elution system is described that includes a radioisotope generator, an eluate tubing line, a radioactivity detector, and a controller. The example specifies that the radioisotope generator is configured to release a radioactive eluate containing a daughter radioisotope during an elution with an eluant the daughter radioisotope being produced from radioactive decay of a parent radioisotope contained within the radioisotope generator. The eluate tubing line is in fluid communication with the radioisotope generator. The example also specifies that the radioactivity detector is positioned to detect a radioactivity of the radioactive eluate while the radioactive eluate is flowing through the eluate tubing line. According to the example, the controller is communicatively coupled to the radioactivity detector and configured to receive data indicative of the radioactivity of the radioactive eluate generated during the elution thereby providing a radioactivity profile of the radioactive eluate relative to at least one of a time during the elution and a volume of radioactive eluate generated during the elution. The controller is further configured to determine a characteristic of the radioactivity profile indicative of breakthrough of the parent radioisotope into the radioactive eluate.

In another example, an elution system is described that includes a radioisotope generator, an eluate tubing line, a radioactivity detector, and a controller. The example specifies that the radioisotope generator is configured to release a radioactive eluate containing a daughter radioisotope during an elution with an eluant the daughter radioisotope being produced from radioactive decay of a parent radioisotope contained within the radioisotope generator. The eluate tubing line is in fluid communication with the radioisotope generator. The example also specifies that the radioactivity detector is positioned to detect a radioactivity of the radioactive eluate while the radioactive eluate is flowing through the eluate tubing line. According to the example, the controller is communicatively coupled to the radioactivity detector and configured to receive data indicative of the radioactivity of the radioactive eluate generated during the elution thereby providing a radioactivity profile of the radioactive eluate relative to at least one of a time during the elution and a volume of radioactive eluate generated during the elution. The example further specifies that the controller is configured to determine a characteristic of the radioactivity profile indicative of breakthrough of the parent radioisotope into the radioactive eluate and compare the determined characteristic of the radioactivity profile indicative of breakthrough to a breakthrough threshold for the characteristic. The example states that the controller is further configured to issue a user alert and/or not allow a patient infusion, if the determined characteristic exceeds the breakthrough threshold.

The details of one or more examples are set forth in the accompanying drawings and the description below. Other features, objects, and advantages will be apparent from the description and drawings, and from the claims.

DETAILED DESCRIPTION

Figure 1:
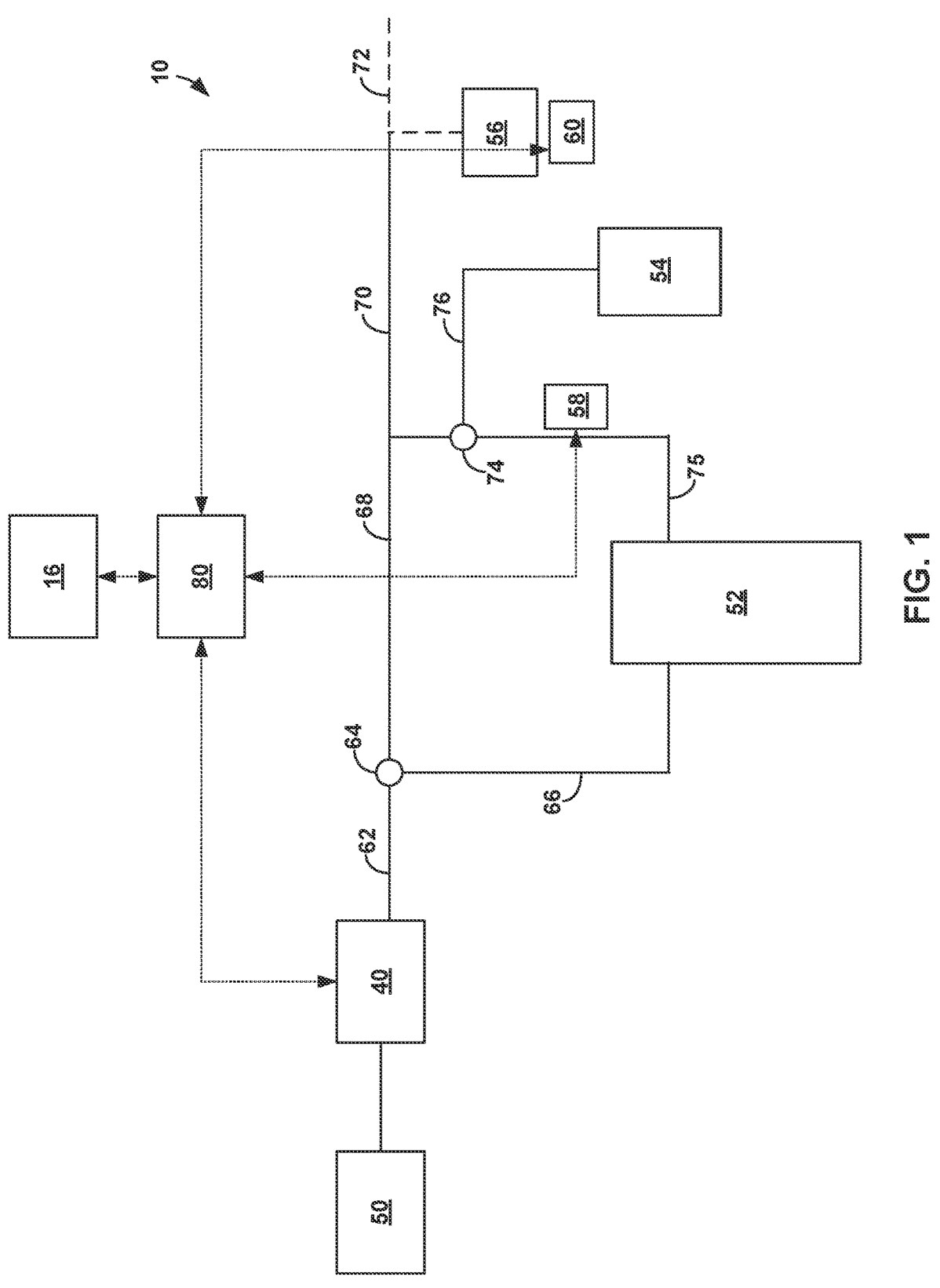
FIG. 1 is a block diagram illustrating an example radiopharmaceutical delivery system.

In general, some embodiments of the present invention relate to early, predictive detection of breakthrough of a parent radioisotope in a radioactive eluate generated via elution of a radioisotope generator. Breakthrough may occur when the parent isotope is detected in eluate generated via elution of the radioisotope generator at a level at or exceeding a threshold corresponding to breakthrough, which is typically a threshold where the eluate is no longer deemed desirable for administration to a patient. In accordance with some examples of the present disclosure, a radioisotope generator system can monitor the radioactivity of radioactive eluate produced by the generator system during one or more elutions. One or more characteristics of the radioactivity profile of the radioactive eluate can be determined and, optionally, compared to corresponding threshold values for those one or more characteristics corresponding to breakthrough. For example, a threshold value may be set based on what the value is when breakthrough occurs but may also include an additional safety factor or margin as part of the threshold.

In either case, the radioisotope generator delivery system may optionally take various actions based on comparison of the current magnitude of the characteristic of the radioactivity profile relative to the threshold value corresponding to breakthrough. As one example, the radioisotope generator delivery system may issue a user alert. The user alert may inform the user that the generator is at or approaching breakthrough. For example, the user alert may indicate an estimated number of elutions (and/or patient administrations) that may be performed before breakthrough is expected to be reached. Additionally or alternatively, the radioisotope generator system may be computer controlled to take certain actions, such as not allowing a patient infusion to be performed if the characteristic of the radioactivity profile indicates that breakthrough has occurred or is likely to occur.

In accordance with some example systems and techniques described herein, the eluate produced by the radioisotope generator is measured to track the radioactive activity of the eluate produced by the generator. Additionally, the amount of time that has passed (e.g., from the start of elution until the end of elution) during which the radioactivity of the eluate is measured may be tracked and/or the volume of eluent pumped into the radioisotope generator (e.g., volume of eluate produced by the radioisotope generator) may be measured or otherwise determined during the period when the radioactivity eluate is measured. This can allow a radioactivity profile for the radioactive eluate to be generated, where the profile corresponds to the measured radioactivity of the eluate relative to the tracked time or volume. A derivative of the profile may also be generated, e.g., to look at a rate of change of the radioactivity profile relative to elution time or elution volume. In either case, one or more characteristics of a profile corresponding to radioactivity of the eluate produced by the radioactivity generator relative to time or volume can be determined, with each such characteristic providing a value that changes during successive elutions, e.g., until breakthrough is observed.

FIG. 1 is a block diagram illustrating an example radioisotope generator system 10 in which the radioactivity activity of the eluate produced by the generated may be measured and tracked along with (1) an amount of time occurring over the elution, (2) a volume of eluent pumped through the radioisotope generator over the elution, and/or (3) a volume of eluate produced by the radioisotope generator over the elution. In the example, system 10 includes an eluant reservoir 50, an eluant pump 40, a radioisotope generator 52, a waste container 54, an eluate-receiving reservoir 56, a controller 80, and a user interface 82. System 10 also includes at least one radioactivity detector, which is illustrated as being implemented using two radioactivity detectors: a beta detector 58 and a gamma detector 60. One or more fluid tubing lines can connect the various components of system 10 together.

For example, in the configuration of FIG. 1, pump 40 receives eluant from eluant reservoir 50, pressurizes the eluant, and discharges pressurized eluant into an eluant line 62. A first diverter valve 64 controls the flow of eluant to one of a radioisotope generator inlet line 66 and a radioisotope generator bypass line 68. Eluant flowing through radioisotope generator bypass line 68 bypasses radioisotope generator 52 and can flow directly into an infusion tubing line 70. Infusion tubing line 70 can be in fluid communication with either eluate-receiving container 56 (e.g., during a quality control procedure) or a patient catheter 72 (e.g., during a patient infusion procedure). A second multi-way valve 74 controls a flow of eluate generated by elution within radioisotope generator 52 and received from a radioisotope generator discharge line 75 to either the infusion tubing line 70 or a waste line 76. Waste line 76 can be connected to waste container 54.

During operation, radioisotope generator 52 can generate eluate containing radioisotopes. For example, radioisotope generator 52 may be a strontium-rubidium generator containing strontium-82 bound on a support material, such as stannic oxide or tin oxide. Rubidium-82 is a daughter decay product of strontium-82 and binds less strongly to the support material than the strontium. As pressurized eluant from eluant reservoir 50 is passed through the radioisotope generator, the eluant may release rubidium-82 so as to generate a radioactive eluate. For example, when the eluant is a saline (NaCl) solution, sodium ions in the saline can displace rubidium in the generator so as to elute a rubidium-82 chloride solution.

In other examples, radioisotope generator 52 can generate eluate containing different types of decay products besides rubidium-82. The type of daughter decay product produced by radioisotope generator 52 can be controlled by selecting the type of radioisotope loaded onto the generator support material. Example types of radioisotope generators that can be used as radioisotope generator 52 include, but are not limited to, $^{99}$Mo/$^{99m}$Tc (parent molybdenum-99 bound on a support material to produce daughter decay product technetium-99m); $^{90}$Sr/$^{90}$Y (parent strontium-90 bound on a support material to produce daughter decay product yttrium-90); $^{188}$W/$^{188}$Re (parent tungsten-188 bound on a support material to produce daughter decay product rhenium-188); and $^{68}$Ge/$^{68}$Ga (parent germanium-68 bound on a support material to produce daughter decay product gallium-68). Yet other parent-daughter pairs that can be used as radioisotope generator 52 include: $^{42}$Ar/$^{42}$K; $^{44}$Ti/$^{44}$Sc; $^{52}$Fe/$^{52m}$Mn; $^{72}$Se/$^{72}$As; $^{83}$Rb/$^{83m}$Kr; $^{103}$Pd/$^{103m}$Rh; $^{109}$Cd/$^{109m}$Ag; $^{113}$Sn/$^{113m}$In; $^{118}$Te/$^{118}$Sb; $^{132}$Te/$^{132}$I; $^{137}$Cs/$^{137m}$Ba; $^{140}$Ba/$^{140}$La; $^{134}$Ce/$^{134}$La; $^{144}$Ce/$^{144}$Pr; $^{140}$Nd/$^{140}$Pr; $^{166}$Dy/$^{166}$Ho; $^{167}$Tm/$^{167m}$Er; $^{172}$Hf/$^{172}$Lu; $^{178}$W/$^{178}$Ta; $^{191}$Os/$^{191m}$Ir; $^{194}$Os/$^{194}$Ir; $^{226}$Ra/$^{222}$Rn; and $^{225}$Ac/$^{213}$Bi.

To measure the radioactivity of one or more radioisotopes in the radioactive eluate generated via elution in system 10, the system may include one or more activity detectors configured to receive and measure different radioactive emissions produced by the radioactive eluate. For example, as shown in the example of FIG. 1, system 10 may include a beta detector 58 and a gamma detector 60. Beta detector 58 can be positioned downstream of radioisotope generator 52 to measure beta emissions emitted by radioactive eluate produced by the generator. Gamma detector 60 can also be positioned downstream of radioisotope generator 52 to measure gamma emissions emitted by the radioactive eluate produced by the generator. In other configurations, system 10 may only include a single detector or type of detector (e.g., one or multiple beta detectors, or one or multiple gamma detectors).

The specific locations of beta detector 58 and gamma detector 60 can vary. However, in the example of FIG. 1, beta detector 58 is positioned between an outlet of radioisotope generator 52 and second multi-way valve 74, which is upstream of waste container 54 and infusion tubing 70 along the fluid pathway from the radioisotope generator. By contrast, gamma detector 60 is positioned downstream of the outlet of the radioisotope generator 52 and beta detector 58. For example, gamma detector 60 may be positioned downstream of the second multi-way valve 74 along the fluid pathway of infusion tubing 70.

In operation, beta detector 58 can measure beta emissions emitted by radioactive eluate generated by and discharged from radioisotope generator 52. In some examples, beta detector 58 is positioned in close proximity to radioisotope generator discharge line 75 such that the beta detector can detect beta emissions emitted from radioactive eluate present in the discharge line. The radioactive eluate may be flowing through the radioisotope generator discharge line 75 toward infusion tubing 70 and/or waste line 76. Alternatively, the radioactive eluate may be supplied to the radioisotope generator discharge line 75 and held static (non-flowing) while the beta detector 58 measures beta emissions emitted from the radioactive eluate. In yet other configurations, an eluate-receiving reservoir may be provided in fluid communication with radioisotope generator discharge line 75, for example via an additional multi-way valve, and beta detector 58 positioned to measure beta emissions from the radioactive eluate supplied to the eluate-receiving reservoir. In any configuration, beta detector 58 may measure beta emissions from radioactive eluate generated by the generator in order to detect and/or quantify one or more radioisotopes present in the radioactive eluate.

System 10 also includes a gamma detector 60. In operation, gamma detector 60 can measure gamma emissions emitted by radioactive eluate generated by and discharged from radioisotope generator 52. For example, radioactive eluate generated by radioisotope generator 52 may be discharged through radioisotope generator discharge line 75, diverter valve 74, infusion tubing 70, and supplied to eluate-receiving container 56. Gamma detector 60 may be positioned in close proximity to eluate-receiving container 56 in order to detect gamma emissions emitted by the portion of radioactive eluate delivered to the receiving container. For example, a clinician may attach an outlet of infusion tubing 70 to an inlet of eluate-receiving container 56 in order to supply radioactive eluate to the receiving container. Upon subsequently controlling pump 40 to generate radioactive eluate that is supplied to the eluate-receiving container 56, gamma detector 60 may measure gamma emissions emitted by the radioactive eluate.

While FIG. 1 illustrates one example location for gamma detector 60, other locations may be used. For example, gamma detector 60 may be positioned in close proximity to a tubing line downstream of radioisotope generator 52, such as radioisotope generator discharge line 75 and/or infusion tubing 70. In these examples, gamma detector may measure gamma emissions emitted by radioactive eluate flowing through the tubing line or a static (non-flowing) portion of radioactive eluate held within the tubing line. Independent of the specific location of the gamma detector within system 10, gamma detector 60 may measure gamma emissions from radioactive eluate generated by the radioisotope generator 52 in order to detect and/or quantify one or more radioisotopes present in the radioactive eluate.

For example, gamma emissions measured by gamma detector 60 may be used to detect and/or quantify one or more contaminating radioisotopes in radioactive eluate generated by radioisotope generator 52, while beta emissions measured by beta detector 58 may be used to detect and/or quantify one or more radioisotopes in the radioactive eluate targeted for patient infusion. In some examples, beta detector 58 measures beta emissions from radioactive eluate flowing through radioisotope generator discharge line 75 toward eluate-receiving container 56. Once the radioactive eluate has passed beta detector 58 and filled eluate-receiving container 56, either partially or fully, gamma detector 60 may measure gamma omissions from that portion of radioactive eluate supplied to the receiving container. In these applications, gamma detector 60 may measure gamma emissions from a portion of radioactive eluate also emitting beta emissions which were detected by beta detector 58 as the radioactive eluate flowed towards the eluate-receiving container 56. In other operational configurations, beta detector 58 and gamma detector 60 may not measure radioactive emissions from the same portion or volume of radioactive eluate but may measure radioactive emissions from different portions of radioactive eluate.

Radioisotope generator system 10 in the example of FIG. 1 also includes a controller 80. Controller 80 may be communicatively coupled (e.g., via a wired or wireless connection) to the various pump(s), valves, and other components of system 10, including beta detector 58 and gamma detector 60, so as to send and receive electronic control signals and information between controller 80 and the communicatively coupled components. For example, controller 80 may receive data generated by beta detector 58 indicative of the magnitude of beta emissions detected by the detector. Controller 80 may further receive data generated by gamma detector 60 indicative of the amount and type (e.g., spectral distribution) of gamma emissions detected by the detector. Controller 80 may further process the data to determine an activity of different radioisotopes in the eluate from which beta detector 58 and gamma detector 60 detected beta emissions and gamma emissions, respectively.

Controller 80 may also manage the overall operation of radioisotope generator system 10, including initiating and controlling patient dosing procedures, controlling the various valves and pump(s) in the system, receiving and processing signals from beta detector 58 and gamma detector 60, and the like.

In operation, beta detector 58 can detect beta emissions emanating from radioactive eluate positioned facing the detector. Beta detector 58 can include a variety of components to detect and process beta emission signals. In some configurations, beta detector 58 is implemented using a solid-state detector element such as a PIN photodiode. In these configurations, the solid-state detector element can directly convert impinging radioactive energy into electrons in the semiconductor material of the detector. The electrons can then be amplified into a usable signal (e.g., received by controller 80). In some examples, beta detector 58 includes a scintillator, which converts impinging radioactive energy into light pulses, which are then captured by an attached photon-to-electron converter such as a photomultiplier tube or avalanche photodiode. The choice of the scintillator can determine the sensitivity and the countrate performance. For example, beta detector 58 may be implemented using a plastic scintillator when high sensitivity and high countrate performance are desired.

During operation, gamma detector 60 can detect gamma ray emissions emanating from a portion of eluate positioned in close proximity to the detector, e.g., statically positioned in eluate-receiving container 56 and/or flowing through a tubing line positioned in front of the gamma detector. Gamma detector 60 may include a variety of different components to detect and process gamma ray radiation signals, such as a pulse sorter (e.g., multichannel analyzer), amplifiers, rate meters, peak position stabilizers, and the like. In one example, gamma detector comprises a scintillation detector. In another example, gamma detector comprises a solid-state semiconductor detector.

The specific type of gamma detector selected for detector 60 can vary based on a variety of factors such as, e.g., the required resolution of the detector, the physical requirements for practically implementing the detector in a system (e.g., cooling requirements), the expected sophistication of the personnel operating the detector, and the like. In some applications, gamma detector 60 is a non-ion-chamber type gamma detector (e.g., a detector that measures gamma emissions and does not include an ion chamber). In some applications, gamma detector 60 is a scintillator-type detector, such as a comparatively low-resolution alkali halide (e.g., NaI, CsI) or bismuth germanate (e.g., $Bi_4Ge_3O_{12}$, or BGO). In other applications, gamma detector 60 incorporates a higher-Z metallic species. An example is lutetium oxyorthosilicate, $Lu_2(SiO_4)O(Ce)$ or LSO, which, though slightly better in resolution than BGO, may have limited applicability because of its relatively high intrinsic radiation. As another example, gamma detector 60 may be a cerium-doped lanthanum, such as $LaCl_3(Ce)$ or $LaBr_3(Ce)$.

In other applications, gamma detector 60 is a solid-state semiconductor-type detector, such as a planar germanium detector. For instance, as another example, gamma detector 60 may be a solid-state semiconductor-type telluride detector, such as cadmium-telluride or cadmium-zinc-telluride semiconductor detector. Gamma detector 60 may be operated at room (ambient) temperature or may be cooled below room temperature (e.g., by a cooling device incorporated into radioisotope generator system 10) to increase the resolution of detector.

Gamma detector 60 can generate gamma ray spectroscopy data. For example, the detector may include a passive material that waits for a gamma interaction to occur in the detector volume. Example interactions may be photoelectric effects, Compton effects, and pair production. When a gamma ray undergoes a Compton interaction or pair production, for instance, a portion of the energy may escape from the detector volume without being absorbed so that the background rate in the spectrum is increased by one count. This count may appear in a channel below the channel that corresponds to the full energy of the gamma ray.

A voltage pulse produced by gamma detector 60 can be shaped by a multichannel analyzer associated with the detector. The multichannel analyzer may take a small voltage signal produced by the detector, reshape it into a Gaussian or trapezoidal shape, and convert the signal into a digital signal. The number of channels provided by the multichannel analyzer can vary but, in some examples, is selected from one of 512, 1024, 2048, 4096, 8192, or 16384 channels. The choice of the number of channels may depend on the resolution of the system, the energy range being studied, and the processing capabilities of the system.

Data generated by gamma detector 60 in response to detecting gamma ray emissions may be in the form of a gamma ray spectrum that includes peaks. The peaks may correspond to different energy levels emitted by different radioisotopes within an eluate sample under analysis. These peaks can also be called lines by analogy to optical spectroscopy. The width of the peaks may be determined by the resolution of the detector, with the horizontal position of a peak being the energy of a gamma ray and the area of the peak being determined by the intensity of the gamma ray and/or the efficiency and sensitivity of the detector.

During operation, controller 80 may receive data generated by beta detector 58 and/or gamma detector 60 indicative of beta emissions and gamma emissions detected by the respective detectors. Controller 80 may process the data to determine an activity of one or more radioisotopes in the radioactive eluate from which beta detector 58 and/or gamma detector 60 detected beta emissions and/or gamma emissions, respectively. Controller 80 may manage operation of system 10 based on the determined activity of the one or more radioisotopes. For example, controller 80 may use the radioactivity measured by the beta detector 58 and/or gamma detector 60 to determine a breakthrough characteristic for the radioactivity profile.

System 10 can operate in a number of different modes, including a patient infusion mode and a quality control mode. During a patient infusion procedure, an infusion tubing circuit (e.g., infusion tubing 70) can connect an outlet of the radioisotope generator to a patient catheter. The infusion tubing circuit can be positioned adjacent the beta detector such that, as eluate flows through the infusion tubing circuit, the eluate passes over the beta detector. Beta emissions emitted by the eluate can be detected by the beta detector and the activity of a radioisotope associated with those beta emissions determined.

During a quality control procedure, by contrast, an infusion tubing line (e.g., infusion tubing 70) in fluid communication with the outlet of the radioisotope generator may be attached to the eluate-receiving container instead of a patient catheter. During this quality control procedure, the radioisotope generator may produce radioactive eluate that flows through the tubing line, past the beta detector, and into the eluate-receiving container. The beta detector may measure beta emissions from the radioactive eluate as it flows through the infusion tubing, e.g., to determine an activity level of rubidium-82 in the eluate. The gamma detector may receive gamma emissions from eluate in the eluate-receiving container, e.g., to determine an activity level of a radioisotope of interest (e.g., parent radioisotope) such as strontium-82, strontium-85, and/or other contaminants in the eluate.

For example, when radioisotope generator 52 is implemented using a strontium-rubidium radioisotope generator, controller 80 may receive data from beta detector 58 indicative of beta emissions measured from radioactive eluate flowing through radioisotope generator discharge line 75. Controller 80 may not be able to resolve different radioisotopes from the beta emissions measured by beta detector 58 but may instead be programmed to assume that all such beta emissions are attributable to radioactive rubidium-82 present in the radioactive eluate, since rubidium may be expected to be the predominant radioactive species present. Accordingly, with reference to data stored in memory, controller 80 may determine an activity of rubidium present in the radioactive eluate supplied from radioisotope generator 52 based on a cumulative magnitude of beta emissions measured by beta detector 58.

Controller 80 may further receive in such examples data from gamma detector 60 indicative of gamma emissions measured from a portion of radioactive eluate supplied to eluate-receiving container 56 and/or flowing through a tubing line (in implementations where gamma detector 60 is used to measure gamma emissions from a flowing portion of eluate). Controller 80 may determine which species of one or more other radioisotopes are present in the radioactive eluate and/or an activity level of those species based on the received data from the gamma detector. For example, controller 80 may determine which species of radioisotopes and/or an activity of those radioisotopes are present in the radioactive eluate based on the amount and type (e.g., spectral distribution) of gamma emissions detected by gamma detector 60. For instance, controller 80 may determine an activity of strontium-82 and/or strontium-85 present in the radioactive eluate, if any, which can be contaminants to the rubidium-82 radioisotope intended for patient infusion procedure. Controller 80 may determine a total or cumulative radioactivity for the radioactive eluate based on emissions of all radioisotopes present in the radioactive eluate.

Independent of whether the activity of the radioactive eluate is measured using beta detector 58, gamma detector 60, and or a combination thereof, controller 80 may store data indicative of the measured activity of the radioactive eluate. The data may be stored in a non-transitory computer readable memory associated with the controller. The activity may be stored in the form of one or more values and may be stored in a table or other data structure usable by controller 80. Controller 80 may track the activity of the radioactive eluate storing values indicative of the radioactive activity measure during elution (e.g., from a start of elution when radioactive eluate begins flowing through an eluate tubing line and is measured by a radioactivity detector to an end of elution when the radioactive eluate ceases flowing through the eluate tubing line). Controller 80 may track the activity of the radioactive eluate over a single elution or over multiple solutions (e.g., all elutions of the radioisotope generator).

Controller 80 can also track a cumulative volume of eluent pumped into radioisotope generator 52 during each elution and/or a cumulative volume of eluate generated by radioisotope generator 52 during each elution. In general, the volume of eluant introduced into radioisotope generator 52 is the same as the volume of eluate produced by the generator. Accordingly, controller 80 may track the cumulative volume of radioactive eluate generated by radioisotope generator 52 by tracking the eluate itself and/or by tracking the volume of eluant supplied to the radioisotope generator, thereby deriving the volume of radioactive eluate generated by radioisotope generator 52.

In some examples, system 10 includes one or more volume sensors (e.g., flow rate sensors) that measure the volume of eluant introduced into generator 52 and/or eluate discharging from the generator. Controller 80 can receive a signal from the one or more volume sensors indicative of the volume of eluate produced by radioisotope generator 52. Additionally or alternatively, controller 80 may receive information indicative of a volume of eluant pumped by pump 40 which, in turn, provides data concerning the volume of eluent pumped into the generator and/or the volume of eluate produced by generator 52.

Pump 40 may be implemented as a syringe pump, peristaltic pump, piston pump, or yet other fluid conveyance device, e.g., with a motor driving the pump. Controller 80 may receive a signal from a displacement sensor monitoring a position of pump 40 (and hence the corresponding volume expected to be delivered by the pump based on position), a sensor monitoring an amount of electrical power (e.g., current) drawn by the motor of pump 40 during operation (and hence the corresponding volume expected to be delivered by the pump based on the power), and/or other information concerning the volume of fluid moved by pump 40 into and through radioisotope generator 52.

Controller 80 may track the cumulative volume of eluent pumped into radioisotope generator 52 and/or the cumulative volume of eluate produced by radioisotope generator 52 during each elution by storing one or more values indicative of the volume in a non-transitory computer readable memory associated with the controller. Controller 80 may track the cumulative volume by generating a sum or total volume of eluate generated by radioisotope generator 52 during each elution (e.g., where each elution starts with a zero volume at the beginning of elution and proceeds to a final volume at the end of the elution). The volume may be stored in the form of one or more values and may be stored in a table or other data structure usable by controller 80.

Additionally or alternatively, controller 80 can track a cumulative time over which elution occurs during each elution of radioisotope generator 52. System 10 may include or be communicatively coupled to a clock or other time measurement instrument. Controller 80 may generate a timestamp when each elution begins and a timestamp when each elution ends, allowing the cumulative amount of time over the course of elution to be calculated. Additionally or alternatively, controller 80 may start a counter upon the start of elution that incrementally increases with increasing time over the course of elution and terminate the counter upon the end of elution. Controller 80 may track the amount of time that passes during each elution by storing one or more values indicative of the time in a non-transitory computer readable memory associated with the controller. The time may be stored in the form of one or more values and may be stored in a table or other data structure usable by controller 80.

As briefly discussed above, radioisotope generator 52 may release one or more radioisotopes into the eluate that is undesired (e.g., is not targeted for injection into a patient for clinical use). The activity of these one or more undesired radioisotopes released into the eluate may increase over the operational life of radioisotope generator 52. Initially, the activity of the undesired radioisotope in the eluate produced by radioisotope generator 52 may be sufficiently low that the eluate produced by the generator is suitable for introduction into a human patient. Over continued service with successive elutions, the activity of the undesired radioisotope in the eluate produced by radioisotope generator 52 may increase to a level where it is unsuitable to be introduced into a patient. This level may be referred to as breakthrough.

The specific threshold(s) at which the activity level of the undesired radioisotope(s) in the eluate produced by radioisotope generator 52 reach (e.g., equal and/or exceed) to be unsuitable for injection into a patient may vary, e.g., depending on the type of generator used. In the case of a Sr-82/Rb-82 radioisotope generator that produces radioactive rubidium-82 from a radioisotope generator containing strontium-82, the threshold may be a Sr-82 level of less than 0.05 µCi per millicurie of Rb-82, such as less than 0.02 µCi per millicurie of Rb-82, about 0.02 µCi per millicurie of Rb-82, less than 0.01 µCi per millicurie of Rb-82, or about 0.01 µCi per millicurie of Rb-82. For example, the threshold may be a strontium-82 activity less than 0.02 µCi, such as a strontium-82 activity between 0.002 µCi and 0.02 µCi, or a strontium-82 activity of 0.01. Additionally or alternatively, the threshold may be a Sr-85 level of 0.5 µCi per millicurie of Rb-82, such as less than 0.2 µCi per millicurie of Rb-82, about 0.2 µCi per millicurie of Rb-82, less than 0.1 µCi per millicurie of Rb-82, or about 0.1 µCi per millicurie of Rb-82. Any threshold may be stored in a memory associated with controller 80.

Controller 80 can determine one or more characteristics indicative of breakthrough of a parent radioisotope in the radioactive eluate produced by radioisotope generator system 10 based on analysis of the radioactivity profile of the radioactivity eluate generated by radioisotope generator 52. It is understood that the radioactivity of the radioactive eluate is largely or completely attributed to the radioactivity of the daughter isotope although a very small amount of radioactivity may be attributed to the parent radioisotope, especially when the radioisotope generator is near or past breakthrough. The radioactivity measurement information of the radioactive eluate tracked by controller 80 during an elution can be correlated to corresponding time information and/or volume information also tracked by the controller during the elution. This can provide a radioactivity profile for the radioactive eluate, e.g., with the measured radioactivity of the radioactive eluate providing one coordinate and a corresponding time or volume providing a second coordinate to yield a two-coordinate data point within a Cartesian coordinate system. The radioactivity profile may be defined by plotting tracked activity on a y-axis of a graph with corresponding time or volume data plotted on the x-axis of the graph.

Figure 4:
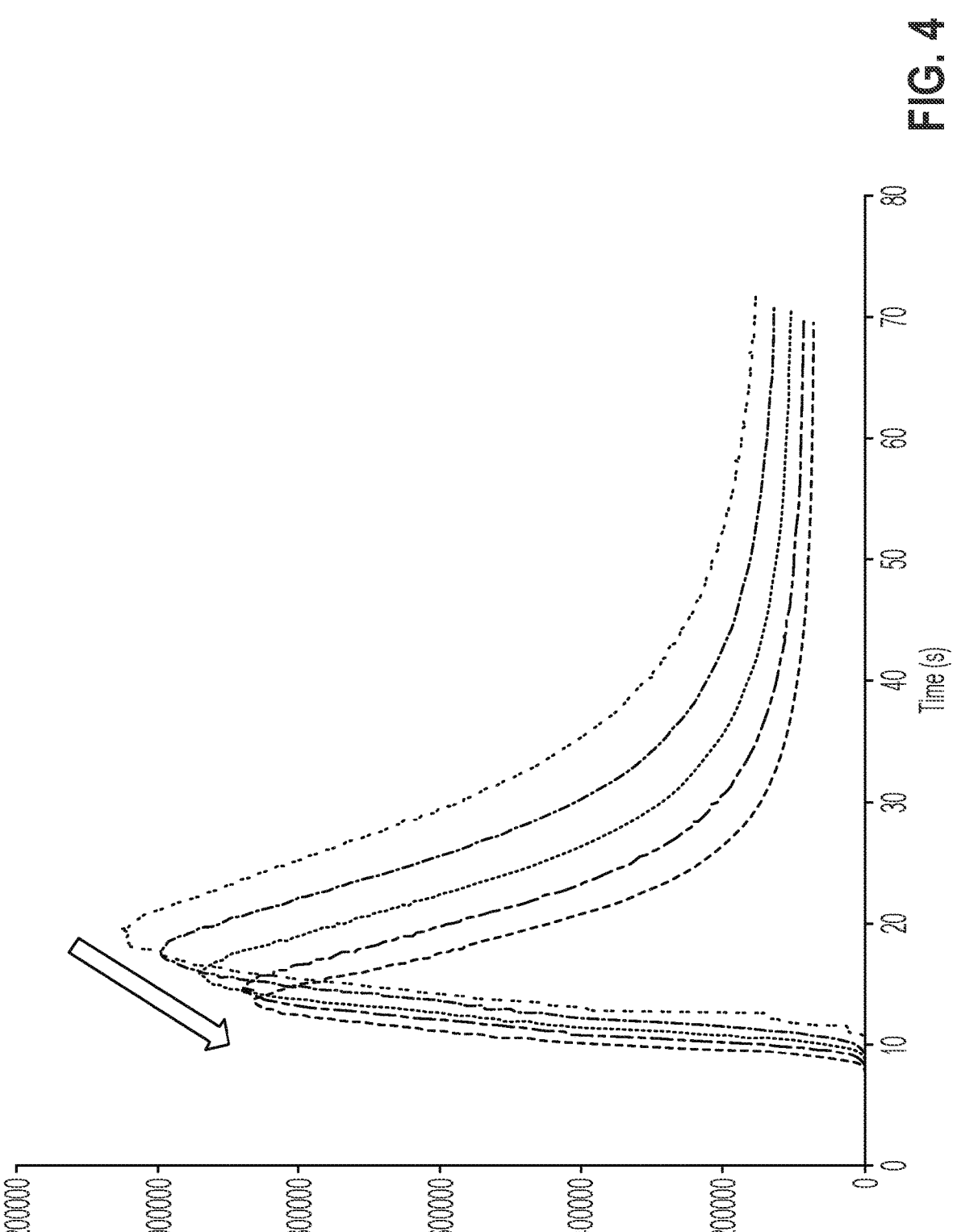
FIG. 4 is a plot illustrating a plurality of example radioactivity profiles, where each radioactivity profile corresponds to a different elution for the radioisotope generator. The radioactivity of the eluate is plotted on the y-axis and the cumulative time over each elution is plotted on the x-axis.

FIG. 4 is a plot illustrating a plurality of example radioactivity profiles, where each radioactivity profile corresponds to a different elution for the radioisotope generator. In this example, the radioactivity of the eluate is plotted on the y-axis and the cumulative time over each elution is plotted on the x-axis. This example illustrates the peak radioactivity shifting earlier in the elution process (to the left on the illustrate graph) over successive elutions.

Controller 80 can determine one or more characteristics indicative of a change in the shape of the radioactivity profile from initial elution to elution when breakthrough occurs. As one example, controller 80 may determine a lapsed time and/or a lapse volume between a start of elution (e.g., a zero time or volume for the radioactivity profile) and a peak radioactivity. Since the peak radioactivity will shift over time and/or successive elutions-either to peak earlier in the elution or later in the elution, depending on the configuration and characteristics of the radioisotope generator system—the amount of time and/or volume that passes until the peak radioactivity is observed can be used as a characteristic indicative of breakthrough.

Additionally or alternatively, controller 80 may determine a lapsed time and/or a lapsed volume between any two levels or points on the radioactivity profile to provide a characteristic of the radioactivity profile indicative of breakthrough (e.g., provided the lapsed time and/or the lapse volume between the two points changes from the first elution using the generator to a subsequent elution when breakthrough occurs). For example, controller 80 may determine an amount of time passed during elution and/or an amount of volume pumped into radioisotope generator 52 or eluted from the generator between when the radioactive eluate was at a first predetermined radioactivity level and when the radioactivity was at a second predetermined radioactivity level. The first predetermined level may be a zero value or nonzero value corresponding to a start of elution, or may be a different value occurring after elution has a started.

The second predetermined level may be a peak (maximum) radioactivity level or may be a different predetermined level. Additionally or alternatively, the second predetermined value may be a percentage of the peak value. For example, the second predetermined level may be of value falling within a range from about 10% of the peak value to about 90% of the peak value, such as from about 20% of the peak value to about 80% of the peak value, from about 25% of the peak value to about 70% of the peak value, or from about 30% of the peak value to about 50% of the peak value. As specific examples, the second predetermined level may be about 10% of the peak value, about 20% of the peak value, about 30% of the peak value, about 40% of the peak value, about 50% of the peak value, about 60% of the peak value, about 70% of the peak value, about 80% of the peak value, or about 90% of the peak value.

Controller 80 may analyze a radioactivity profile defined by the measured radioactivity of the radioactive eluate and/or may analyze a radioactivity profile defined by a derivative of the radioactive to the of the radioactive eluate over elution time or elution volume. For example, controller 80 may determine a first derivative of the radioactivity of the radioactive eluate over time or volume and/or may determine a second derivative of the radioactivity of the radioactive eluate over time or volume.

Figure 5:
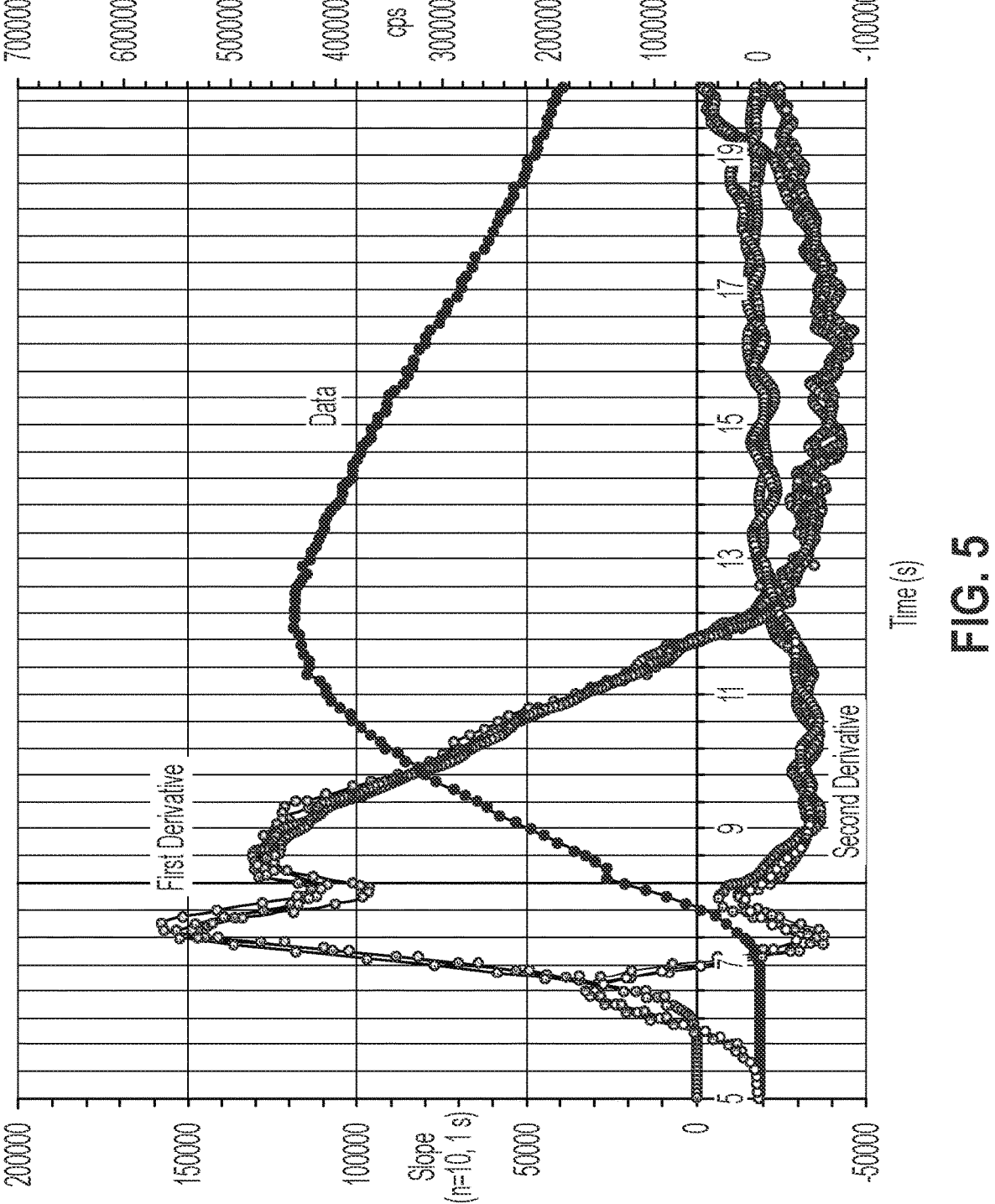
FIG. 5 is a plot illustrating an example radioactivity profile where radioactivity of the eluate is plotted on the y-axis and the cumulative time over each elution is plotted on the x-axis. First and second order derivatives of the raw data are also plotted on FIG. 5 for comparative illustration.

FIG. 5 is an example plot illustrating an example radioactivity profile where radioactivity of the eluate is plotted on the y-axis and the cumulative time over each elution is plotted on the x-axis. First and second order derivatives of the raw data are also plotted on FIG. 5 for comparative illustration.

When controller 80 determines a characteristic of the radioactivity profile indicative of breakthrough, and the radioactivity profile is representative of a derivative of the measured activity itself, the predetermined levels between which the lapsed time and/or the lapse volume is measured may vary as compared to when analyzing the measured radioactivity values themselves. For example, the first and second predetermined levels between controller 80 determines the lapsed time and/or the lapse volume may correspond to predetermined rates of change of the radioactivity rather than absolute values for the radioactivity.

Independent of the specific predetermined levels that controller 80 uses to determine the lapsed time and/or lapse volume characteristic indicative of breakthrough, the one or more levels may be stored in a non-transitory computer readable media associated with the controller. The predetermined levels may be stored in the computer readable media by user via user interface.

In some examples, controller 80 compares the characteristic determined for the radioactivity profile, or a derivative thereof, indicative of breakthrough threshold for the characteristic. The breakthrough threshold for the characteristic may be determined by operating radioisotope generator 52 (or, more practically, a similarly configured radioisotope generator to that deployed in the field) for a successive number of elutions until breakthrough is observed. The radioactivity profiles for the radioisotope generator during such testing can be generated and analyzed to determine values for the characteristic or characteristics of interest during each successive elution. When breakthrough is detected, the value of the characteristic corresponding to the radioactivity profile measured for that elution can be used as the breakthrough threshold in similar configured systems. In some implementations, an additional safety margin may be built into the breakthrough threshold.

Controller 80 may compare the determine characteristic of the radioactivity profile indicative of breakthrough for the system under analysis to the breakthrough threshold for the characteristic by determining a difference between the two values, a ratio between the two values, and/or performing yet other type of comparative analysis. The determined characteristic of the radioactivity profile indicative of breakthrough for the system, at which the activity of an undesired radioisotope in the radioactive eluate will reach a threshold, may be additionally or alternatively analyzed to predict the remaining time and/or volume that can be eluted by the generator before reaching the breakthrough.

If controller 80 determines that the characteristic of the radioactivity profile indicative of breakthrough exceeds the threshold, controller 80 may take a variety of actions. As one example, controller 80 may initiate a user alert (e.g., a visual, textual, audible user alert), e.g., by controlling user interface 16 to deliver the alert concerning the predicted breakthrough and/or remaining volume that can be eluted by the generator before reaching the breakthrough. As another example, controller 80 may terminate elution using radioisotope generator or otherwise prevent a patient infusion procedure (e.g., by controlling pump 40 to cease generating eluate and/or controlling second multi-way valve 74 to divert elute from infusion tubing 70 to waste line 76) when the characteristic of the radioactivity profile indicates breakthrough is occurring or is likely to occur. In some examples, an operator or party responsible with maintaining system 10 may replace radioisotope generator 10 with a fresh generator when the cumulative volume reaches or is within the threshold of the predicted volume.

As the generator is eluted, the characteristic of the radioactivity profile indicative of breakthrough may approach a threshold that exceeds breakthrough in a manner that can be used to detect when abnormal operation of the radiopharmaceutical delivery system is occurring. For instance, if the approach to the threshold is regular (e.g., linear, curved, exponential), a departure from that regularity may indicate abnormal operation. As one example, if the approach to the threshold is linear with elution volume, a departure from linearity may indicate abnormal operation. A linear relationship between two parameters is defined in part by the slope of the line; thus, if the slope changes it may indicate a change in function of the system.

One example scenario that may cause a change in approach to the threshold is when an inappropriate eluent is used during elution. In the case of a strontium-rubidium generator containing strontium-82 bound on a support material, such as stannic oxide or tin oxide, an appropriate eluent may be an additive free 0.9% sodium chloride solution. By contrast, an inappropriate eluent may be one containing elevated divalent cations such as Ca++, Zn++, and the like that compete with Sr++ for binding to the support material. Ringer's or Ringers Lactate solutions are examples of such inappropriate eluents containing elevated levels of divalent cations. An example of an inappropriate eluent may be one that contains insufficient monovalent cations, such as insufficient levels of Na+ in a sodium chloride solution and/or the wrong concentration of protons (pH). In these examples, the slope may increase or decrease relative to normal depending on the eluent.

In a similar manner, the intercept of a linear relationship may also change. The intercept in its own right may provide information on the performance or potential performance of the system. For instance, if the slope of the characteristic of the radioactive profile vs volume is the same for a number of generators but the intercept (x=0) is different, it may suggest that the threshold of the radioactivity profile at breakthrough may be different.

A change in the characteristics of the approach to the breakthrough threshold may also be caused by, for example, a change in the eluent flow rate or the performance of the column due to damage. Such damage may be caused by a physical shock to the column that causes a change in the packing of the column or other causes.

It should be appreciated that while the foregoing computational steps are described as being performed by controller 80 (which also controls system 10), the computing functionality attributed to controller 80 in system 10 may be performed on any one or more controllers associated with the system, be it physically on system 10 or remotely located, and the functionalities described herein are not limited to being performed on any specific hardware device. For example, system 10 and controller 80 may communicate with an external device, such as a remote server, cloud-computing environment, or other physically remote computing device performing some or all of the computing functionality described herein. That being said, in other configurations, one or more controllers located on system 10 (e.g., on a mobile cart or platform associated with components of the system) may perform some or all of the controller functions described herein.

As noted, system 10 may include a user interface 16. User interface 16 may include a display screen as illustrated or other output media, and user input media. For example, user interface may include a keyboard, mouse, depressible buttons, switches, and/or touch screen interface. In some examples, user interface 16 may be configured to provide visual, audible, and/or tactile feedback to a user. User interface 16 may be communicatively coupled to a controller that controls the operation of system 10. A clinician or other user may interact with system 10 through user interface 16, e.g., to change or establish the parameters of a patient infusion procedure, change or establish the parameters of a quality control procedure, view historical or maintenance information, or otherwise interact with system 10. In one example, user interface 16 is implemented as a touchscreen having a screen that a user can physically touch to communicate with system 10.

As further noted above, system 10 may include a waste container 54 and in eluate-receiving container 56. Waste container 54 and eluate-receiving container 56 may each be structures configured to receive and hold liquid received from upstream tubing. In different examples, waste container 54 and/or eluate-receiving container 56 may be reservoirs permanently formed in a shielding assembly containing radioisotope generator 52 or maybe removable from the shielding assembly. For example, waste container 54 and/or eluate-receiving container 56 may be a vessel (e.g., bottle, vial, canister, or other receptacle) configured to receive radioactive eluate, each of which is removable from a shielding assembly containing radioisotope generator 52.

In general, waste container 54 is intended to receive radioactive eluate produced upon activation of system 10, as pump 40 pumps eluant through radioisotope generator 52 toward waste container 54. For example, in operation, pump 40 may pump eluant through radioisotope generator 52 while controller 80 controls second multi-way valve 74 to direct radioactive eluate toward waste container 54. Upon determining that the radioactive eluate produced by radioisotope generator 52 has a threshold level of activity, controller 80 may control second multi-way valve 74 to direct the radioactive eluate to infusion tubing 70 (and to patient catheter 72 or eluate-receiving container 56 coupled thereto) instead of toward waste container 54. Controller 80 may determine that the radioactive eluate produced by radioisotope generator 52 has a threshold level of activity based on the beta emissions measured by beta detector 58, e.g., and threshold information stored in memory associated with the controller. In different examples, waste container 54 may be sized to hold a volume of liquid received from radioisotope generator 52 of at least 100 mL, such as at least 250 mL, or greater than or equal to 500 mL. As one example, waste container 54 may be sized to hold from 250 mL to 1 L.

In contrast to waste container 54 which is intended to receive radioactive eluate produced by radioisotope generator 52 that is designated as waste, eluate-receiving container 56 can receive patient-infusible radioactive eluate produced by the radioisotope generator. Eluate-receiving container 56 may receive and hold a portion of the radioactive eluate produced by the radioisotope generator (e.g., after controller 80 has actuated multi-way valve 74 to redirect the radioactive eluate being produced from waste line 76 to infusion tubing 70). While eluate-receiving container 56 is being filled with radioactive eluate and/or after the eluate-receiving container has filled, gamma detector 60 may measure gamma emissions emanating from the radioactive eluate. In some examples, beta detector 58 measures beta emissions from radioactive eluate flowing through radioisotope generator discharge line 75 as the eluate flows to eluate-receiving container 56, whereupon gamma detector 60 measures gamma omissions from that same portion of eluate whose beta emissions were previously measured by the beta detector.

Controller 80 may determine an activity of one or more radioisotopes present in the radioactive eluate received by an eluate-receiving container 56 based on the gamma emissions measured by gamma detector 60. This activity may be tracked by controller 80 as discussed above to determine a predicted volume of the radioactive eluate generated by the radioisotope generator at which the activity of an undesired radioisotope in the radioactive eluate will reach a threshold.

Although eluate-receiving container 56 can have a number of different configurations, in some examples, the eluate-receiving container is sized smaller than waste container 54. For example, eluate-receiving container 56 may be sized to receive and hold a volume of liquid less than 500 mL, such as less than 250 mL or less than 100 mL. In one example, eluate-receiving container is sized to hold from 10 mL to 100 mL. Further, while eluate-receiving container 54 can be implemented using a variety of different types of containers, in some examples, the eluate-receiving container is fabricated of glass or plastic, such as a glass vial or bottle, or a plastic syringe or container. Such a structure may be useful in that the glass vial may limit the extent to which gamma emissions are blocked or attenuated by the eluate-receiving container, allowing gamma detector 60 to adequately detect gamma emissions emitted by the radioactive eluate delivered to the container.

In practice, eluate-receiving container 56 may be reused for multiple quality control procedures or may be disposable after each quality control procedure. For instance, in some applications, an operator may select a new, previously unused, eluate-receiving container and insert the container into an appropriate compartment of a shielding assembly containing radioisotope generator 52. After performing the quality control procedure, the operator can remove the eluate-receiving container, discard the contents of the container appropriately, and then discard the container itself. Typically, waste container 54 is a reusable structure, for example fabricated from metal, glass, or other compatible material, that may be removed and emptied from a shielding assembly containing radioisotope generator 52 periodically but is not discarded after use.

Some or all of the components of system 10 may be contained within a shielding assembly. The shielding assembly can house various components of system 10 exposed to and/or in contact with radioactive eluate. In general, the shielding assembly may be formed of one or more materials that provide a barrier to radioactive radiation. The type of material or materials used to fabricate the shielding assembly and the thicknesses of those materials may vary, for example, depending on the type and size of radioisotope generator 52 used in the system and, correspondingly, the amount of radiation shielding needed. In general, the thickness and/or configuration of the radiation shielding material used to form the shielding assembly may be effective to attenuate radiation emanating from inside of the shielding assembly to a level which is safe for operating personnel to work around system 10. For example, when a new strontium-rubidium generator is installed in the shielding assembly, it may contain 200 millicuries of radioactivity. The shielding assembly may block the emitted radiation so the radiation level outside of the shielding assembly does not exceed that which is allowable for operating personnel surrounding the shielding assembly and block the ingress of radiation into the detector compartments to keep background radiation at appropriate levels. In some examples, the shielding assembly is fabricated from lead or lead alloys or other high-density materials, e.g., and may have a wall thickness greater than 25 millimeters.

Additionally, in some examples, system 10 (including any shielding assembly) may be installed on a frame that defines a mobile cart frame. For example, the components of system 10 may be physically and/or mechanically connected (directly or indirectly) to a frame that carries the components. The frame may be mounted on wheels so as to be movable. Additional details on some embodiments of radioisotope generator systems that may be used in accordance with the disclosure are described in PCT/US17/52537, filed Sep. 20, 2017, the entire contents of which are incorporated herein by reference.

Figure 2:
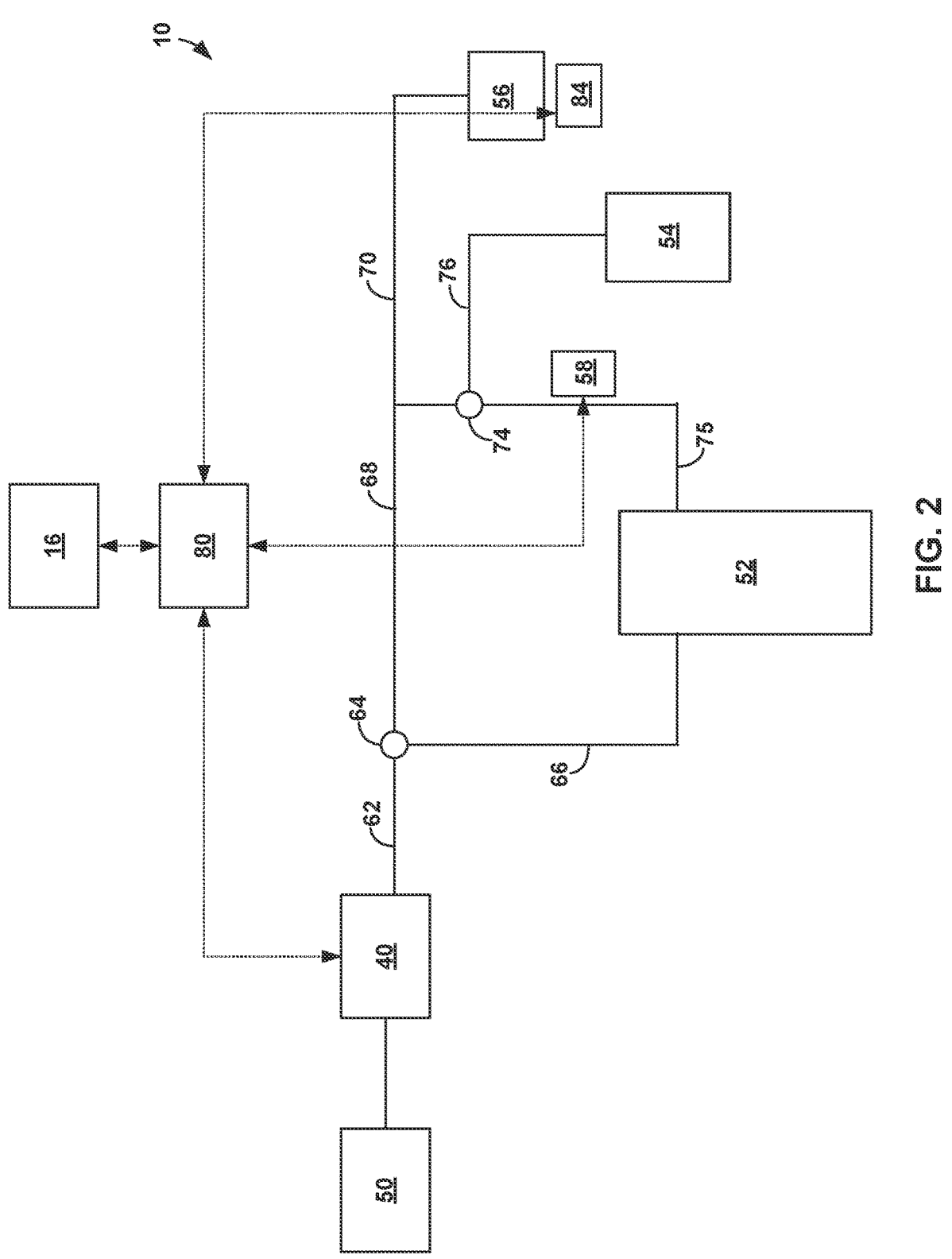
FIG. 2 is a block diagram illustrating another example configuration of an example radioisotope generator system.

FIG. 2 is a block diagram illustrating another example configuration of radioisotope generator system 10 where like reference numerals refer to like elements discussed above with respect to FIG. 1. The example configuration of system 10 in FIG. 2 is different than the configuration in FIG. 1 in that system 10 in FIG. 2 includes a dose calibrator 84 to measure an activity of radioactive eluate produced by radioisotope generator 52 (in addition to or in lieu of beta detector 58) rather than gamma detector 60.

Dose calibrator 84 may be an instrument used to assay the activity of a radioactive material prior to clinical use. The objective of the assay can be to assure that the patient receives the prescribed dose for the diagnostic or therapeutic purpose. A dose calibrator typically includes an electrometer designed to measure a wide range of ionization current, spanning from femtoamperes (fA) for beta emitters up to tens of picoamperes (pA) for high-energy, high-yield photon emitters. Some high-activity assays can even involve microamperes (μA) currents. The accuracy of the electrometer depends upon the type and quality of the electrometer and the accuracy of the standard reference sources used to calibrate the electrometer. Dose calibrators generally have no intrinsic photon energy discrimination capability. Accordingly, dose calibrator may not include a spectrometer and may not restrict the measurement to specific photon energies to the exclusion of others, which gamma detector 60 is capable of performing. For example, dose calibrator 84 may include an ion chamber whereas gamma detector 60 may lack an ion chamber (e.g., be a non-ion-chamber type gamma detector).

Activity measurements made by beta detector 58 may be distinguishable from those made by gamma detector 60 and/or dose calibrator 84. A beta detector can measure beta emissions caused by radioactive beta decay. During beta decay, a beta particle that is either an electron or a positron is emitted from an atomic nucleus. The beta detector can detect beta particles emitted from the radioactive eluate, allowing the activity level of a radioisotope assumed to be associated with those beta particles to be determined. By contrast, gamma detector 60 can measure gamma emissions or photons caused by primary radioactive gamma decay or secondary to the emission and annihilation of positrons. During gamma decay, a stream of high-energy photons may be emitted from an atomic nucleus, providing detectable gamma rays. The energy level of the gamma rays may vary depending on the specific radioisotope from which the rays are emitted. Gamma detector 60 can detect the gamma emissions, for example by measuring a full or partial gamma spectrum, allowing the activity level of one or more radioisotopes to be determined. Further, gamma detector 60 may discriminate photons with different energy levels, unlike dose calibrator 84.

Dose calibrator 84 may be used to determine an activity of one or more undesired radioisotopes in eluate produced by radioisotope generator 52, e.g., for tracking and determination of the predicted volume. Dose calibrator 84 may be external to and separate from the other components of system 10 or may be integrated with the components of the system. For instance, in some examples, infusion tubing line 70 extends from system 10 to an eluate collection container positioned in a dose calibrator 84 located off board a mobile cart (e.g., on a counter or table adjacent to the cart) containing the other components of system. In other configurations, system 10 may include an onboard dose calibrator 84 that is contained on the mobile cart with the other components of the system and is movable therewith. In either case, controller 80 may receive data generated by the dose calibrator via wired or wireless communication with the dose calibrator and/or via user entry using user interface 16.

During quality control testing as discussed above with respect to FIG. 1, controller 80 can control system 10 to deliver radioactive eluate to the eluate collection container.

To initiate the process, an operator may attach infusion tubing line 70 to eluate collection container 56 and interact with system 10 (e.g., via user interface 16) to elute a sample of eluate. The eluate collection container may or may not be inserted into a dose calibrator prior to initiating elution. The activity of the eluate received by the collection container 56 may be measured by dose calibrator 84 continuously from filling of the container through completion of the calibration measurement or at one or more discrete time periods during the quality control process. For example, the activity of the eluate in the container may be measured following the end of elution, when pump 40 ceases pumping eluant through radioisotope generator 52 to generate eluate or controller 80 controls multi-way valve 74 to direct the radioactive eluate to waste container 54 instead of the eluate collection container.

In some examples, dose calibrator 84 measures an activity of eluate supplied to the eluate-receiving container 56 after a period of time sufficient for substantially all the initial daughter radioisotope (e.g., Rb-82) in the radioactive eluate to decay. In some examples, the period of time sufficient for substantially all the initial daughter radioisotope to decay is at least 3 half-lives of the daughter radioisotope, such as at least 5 half-lives of the daughter radioisotope. In the case of Rb-82 which has a half-life of about 76 seconds, the period of time may be greater than 15 minutes, such as greater than 20 minutes, or greater than 30 minutes. For example, the period of time may range from 15 minutes to one hour, such as 25 minutes to 45 minutes. The resulting activity measurement made by dose calibrator 84 may be that of one or more undesired radioisotopes, such as Sr-82 and/or Sr-85 in the case of a Sr-82/Rb-82 radioisotope generator. Controller 80 (or other computing device) may determine the activity of the other strontium radioisotope with reference to a ratio stored in memory relating the activity of Sr-82 to the activity of Sr-85. The activity of Sr-82 may be related to the activity of strontium-85 by a known radioisotope ratio, which may be stored in memory associated with controller 80. Controller 80 can determine the activity of one radioisotope by multiplying the determined activity of the other radioisotope by the stored ratio. In some examples, controller 80 sums the determined activity of Sr-82 and the determined activity of Sr-85 to identify the total strontium activity in the radioactive eluate. In either case, controller 80 can receive the activity information and track the activity information for determining a predicted volume at which the activity of the radioisotope in the radioactive eluate will reach a threshold, as discussed above with respect to FIG. 1.

Figure 3:
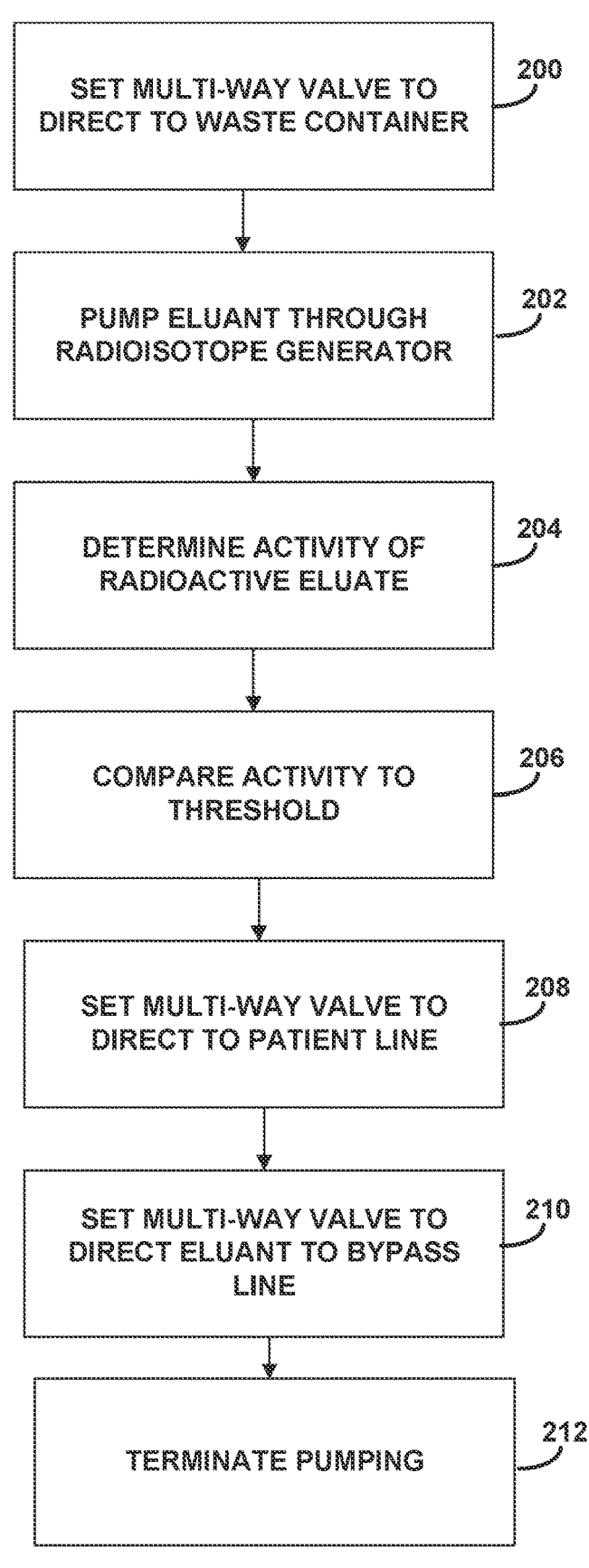
FIG. 3 is a flow diagram of an example technique that may be used to perform a patient infusion procedure to infuse radioactive liquid into a patient.

FIG. 3 is a flow diagram of an example technique that may be used to perform a patient infusion procedure to infuse radioactive liquid into a patient, e.g., during a diagnostic imaging procedure. For example, the technique of FIG. 3 may be used by system 10 to generate radioactive eluate and infuse the radioactive eluate into a patient. The technique of FIG. 3 will be described with respect to system 10, and more particularly the arrangement of exemplary components described with respect to FIG. 1 above, for purposes of illustration. However, it should be appreciated that the technique may be performed by systems having other arrangements of components and configurations (e.g., FIG. 2), as described herein.

To initiate a patient infusion procedure, an operator may interact with system 10 to set the parameters of the infusion and to initiate the infusion procedure. System 10 may receive parameters for the infusion via user interface 16, via a remote computing device communicatively coupled to system 10, or through yet other communication interfaces.

Example parameters that may be set include, but are not limited to, the total activity to be dosed to a patient, the flow rate of radioactive eluate to be dosed to the patient, and/or the volume of radioactive eluate to be dosed to the patient. Once the appropriate parameters establishing the characteristics of the infusion procedure are programmed and stored, system 10 may begin generating radioactive eluate that is infused into the patient.

As shown in the example of FIG. 3, a patient infusion procedure may start by controlling second multi-way valve 74 to place radioisotope generator discharge line 75 in fluid communication with waste container 54 via waste line 76 (200). If second multi-way valve 74 is initially positioned so radioisotope generator discharge line 75 is in fluid communication with waste container 54, controller 80 may control system 10 to proceed with the infusion procedure without first actuating the valve. However, if second multi-way valve 74 is positioned so radioisotope generator discharge line 75 is in fluid communication with infusion tubing 70, controller 80 may control second multi-way valve 74 (e.g., by controlling an actuator associated with the valve) to place the radioisotope generator discharge line in fluid communication with the waste container. In some examples, controller 80 receives a signal from a sensor or switch associated with second multi-way valve 74 indicating the position of the valve and, correspondingly, which line radioisotope generator discharge line 75 is in fluid communication with through the valve.

In addition to or in lieu of controlling second multi-way valve 74, controller 80 may check the position of first multi-way valve 64 and/or control the valve to change the position of the valve before proceeding with the patient infusion procedure. For example, if first multi-way valve 64 is positioned to direct eluant through bypass line 68, controller 80 may control the valve (e.g., by controlling an actuator attached to the valve) to place eluant line 62 in fluid communication with the radioisotope generator inlet line 66. In some examples, controller receives a signal from a sensor or switch associated with first multi-way valve 64 indicating the position of the valve and, correspondingly, which line eluant line 62 is in fluid communication with the valve.

With first multi-way valve 64 positioned to direct eluant through radioisotope generator inlet line 66 and second multi-way valve 74 positioned to direct radioactive eluate from radioisotope generator discharge line 75 to waste container 54, controller 80 can control pump 40 to pump eluant from eluant reservoir 50. Under the operation of controller 80, pump 40 can pump eluant from eluant reservoir 50 through radioisotope generator 52, and thereby generate the radioactive eluate via elution through the generator. In different examples, pump 40 may pump eluant at a constant flow rate or a flowrate that varies over time. In some examples, pump 40 pumps eluant at a rate ranging from 10 milliliters/minute to 100 mL/minute, such as a rate ranging from 25 mL/minute to 75 mL/minute. Radioactive eluate generated typically flows at the same rate as the rate at which pump 40 pumps eluant.

As eluant flows through radioisotope generator 52, a radioactive decay product of a parent radioisotope bound in the generator may release and enter the flowing eluant, thereby generating the radioactive eluate. The type of eluant used may be selected based on the characteristics of the parent and daughter radioisotope and support material used for radioisotope generator 52 and the subsequent intended use. Example eluants that may be used include aqueous-based liquids such as saline (e.g., 0.1-1 M NaCl). For example, in the case of a strontium-rubidium radioisotope generator, a Normal (isotonic) saline may be used as an eluant to elute Rb-82 that has been produced by decay from Sr-82 bound on a support material Radioactive eluate generated by radioisotope generator 52 can be conveyed to beta detector 58, allowing the radioactivity level (also referred to as activity) of the eluate to be determined based on measurements made by the beta detector (204). In some configurations, radioactive eluate is supplied to tubing or a reservoir positioned proximate to beta detector 58, allowing the beta detector to measure beta emissions emanating from a stopped and static volume of fluid positioned in front of the detector. In other configurations, beta detector 58 can detect beta emissions emanating from radioactive eluate flowing through tubing positioned proximate to the detector. For example, beta detector 58 may detect beta emissions emanating from radioactive eluate as the eluate flows through radioisotope generator discharge line 75 to waste container 54. Controller 80 may receive a signal from beta detector 58 indicative of the beta emissions measured by the beta detector.

Controller 80 may determine the activity of the radioactive eluate based on the beta emissions measured by beta detector 58. For example, controller 80 may compare a magnitude of the beta emissions measured by beta detector 58 to calibration information stored in memory relating different beta emission levels to different radioactive eluate activity levels. Controller 80 can then determine the activity of the radioactive eluate with reference to the calibration information and the beta emissions measured by beta detector 58 for the current radioactive eluate flowing through radioisotope generator discharge line 75. With all measurements made by system 10, controller 80 may account for radioactive decay between the radioisotope generator and a respective detector as the radioactive eluate travels through one or more tubing lines, or one detector and another detector and/or a patient and/or eluate-receiving container (e.g., from first measurement to delivery or subsequent measurement).

Because beta emissions from different radioisotopes are not easily distinguishable from each other, controller 80 may not be able to resolve what portion of the measured activity is attributable to one radioisotope as opposed to one or more other radioisotopes that may be present in the radioactive eluate. In instances where the radioactive decay product present in the radioactive eluate is assumed to be the predominant radioisotope species, controller 80 may set the measured activity of the radioactive eluate as the activity corresponding to the radioactive decay product. For example, in the case of a strontium rubidium radioisotope generator, the activity of radioactive eluate determined using beta detector 58 may be assumed to be the activity of Rb-82 present in the radioactive eluate. This is because the activity of any other radioisotopes that are present in the radioactive eluate may be assumed to be significantly (e.g., orders of magnitude) smaller than the activity of Rb-82 present in the radioactive eluate.

In some examples, pump 40 continuously pumps eluant through radioisotope generator and radioactive eluate is delivered to waste container 54 until the activity level of the radioactive eluate reaches a threshold level. As additional eluant is flowed through the radioisotope generator and time progresses, the activity may decrease from the peak activity to an equilibrium. Radioactive eluate generated by radioisotope generator 52 after the generator has been inactive for a period of time may initially have a different activity than radioactive eluate generated during continued elution of the generator. The activity of bolus radioactive eluate produced using generator 52 may follow an activity curve that varies based on the volume of eluant passed through the generator and the time since the start of the elution.

In some examples, radioactive eluate generated by radioisotope generator 52 is supplied to waste container 54 until the radioactive eluate reaches a minimum threshold activity value. The minimum threshold activity value can be stored in a memory associated with controller 80. In operation, controller 80 can compare the current activity of the radioactive eluate produced using generator 52 to the activity stored in memory (206). Controller 80 may determine when to actuate second multi-way valve 74 to direct radioactive eluate from waste container 54 to infusion tubing 70, and correspondingly patient line 72, based on the comparison (208).

Since the peak activity of radioactive eluate generated by radioisotope generator 52 may vary over the service life of the generator, the minimum activity threshold may be set relative to one or more previous elution/infusion procedures performed by the radioisotope generator system. For example, for each elution performed by system 10, controller 80 may store in a memory associated with the controller a peak radioactivity detected during that elution, e.g., as measured via beta detector 58. During a subsequent elution, controller 80 may reference the peak radioactivity, which may also be considered a maximum radioactivity, measured during a prior elution. Controller 80 may use that maximum radioactivity from the prior run as a threshold for controlling the radioisotope generator during the subsequent run. In some examples, the threshold is a percentage of the maximum radioactivity measured during a prior elution run, such as an immediate prior elution run. The immediate prior elution run may be the elution run performed before the current elution run being controlled without any intervening elution having been performed between the two elutions. For example, the threshold may be an activity value falling within a range from 5% to 15% of the magnitude of maximum radioactivity detected during a prior elution run, such as from 8% to 12% of the magnitude of maximum activity, or approximately 10% of the magnitude of the maximum activity. In other examples, the threshold may not be determined based on a prior radioactivity measurement measured using system 10 but may instead be a value stored in a memory associated with controller 80. The value may be set by a facility in charge of system 10, the manufacturer of system 10, or yet other party with control over system 10.

In the example of FIG. 3, controller 80 controls second multi-way valve 74 to divert radioactive eluate from waste container 54 to the patient via infusion tubing 70 and patient line 72 connected to the infusion tubing (210). Upon determining that the activity of radioactive eluate flowing through radioisotope generator discharge line 75 via beta detector 58 has reached the threshold (e.g., equals or exceeds the threshold), controller 80 may control second multi-way valve 74 (e.g., by controlling an actuator associated with the valve) to deliver the radioactive eluate to the patient. Pump 40 may continue pumping the eluant through radioisotope generator 52, thereby delivering radioactive eluate to the patient, until a desired amount of radioactive eluate has been delivered to the patient.

In some examples, the desired amount of radioactive eluate is a set volume of eluate programmed to be delivered to the patient. Controller 80 can determine the volume of radioactive eluate delivered to the patient, e.g., based on knowledge of the rate at which pump 40 pumps and the duration the pump has pumped radioactive eluate. Additionally or alternatively, system 10 may include one or more flow sensors providing measurements to controller 80 concerning the volume of eluant and/or volume of radioactive eluate flowing through one or more tubing lines of the system.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a non-transitory computer-readable medium, such as a computer-readable storage medium, containing instructions. Instructions embedded or encoded in a computer-readable storage medium may cause a programmable processor, or other processor, to perform the method, e.g., when the instructions are executed. Non-transitory computer readable storage media may include volatile and/or non-volatile memory forms including, e.g., random access memory (RAM), magnetoresistive random access memory (MRAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

The following examples may provide additional details about radiopharmaceutical delivery systems and techniques in accordance with the disclosure.

Example 1: Successive Generator Elutions to Obtain Bolus Curves

A CardioGen-82 strontium-rubidium radioisotope generator system from Bracco Diagnostics, Inc. of Monroe Township, NJ was used to generate a successive series of elutions over a period of 42 days. The first elution was generated on the first date the $Sr^{82}$—$Rb^{82}$ generator was installed in the system, which was designated day 1. The generator was eluted using saline as an eluant. The activity of the eluate produced during each elution was measured using a CZT gamma detector.

Figure 6:
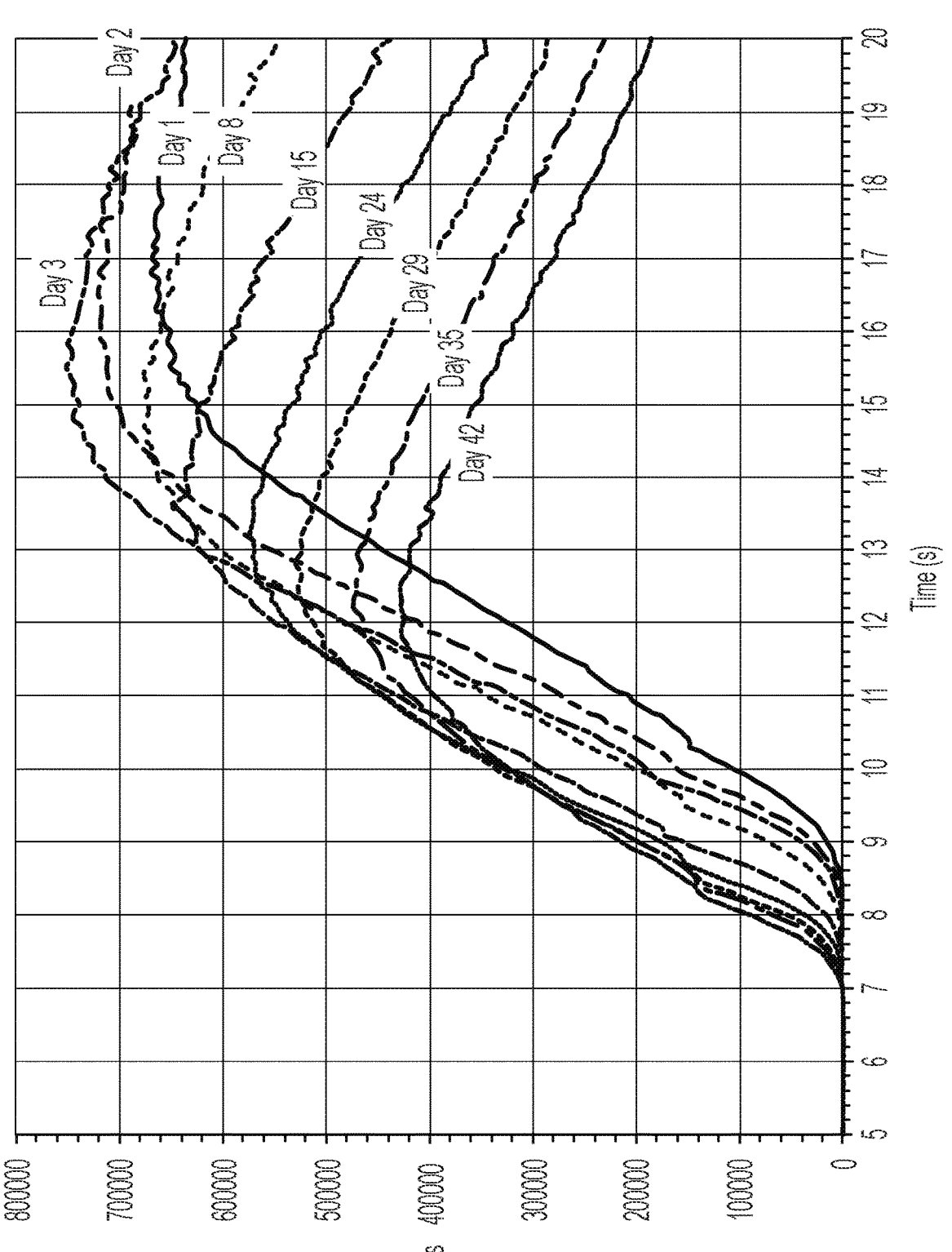
FIG. 6 is a plot of radioactivity profile data for different elutions generated by a radioisotope generator on different days.

FIG. 6 is a plot of the radioactivity profiles of different elutions generated by the generator on different days. The radioactivity of the eluate is plotted on the y-axis in counts per second (cps). The time over each elution is plotted on the x-axis.

Figure 7:
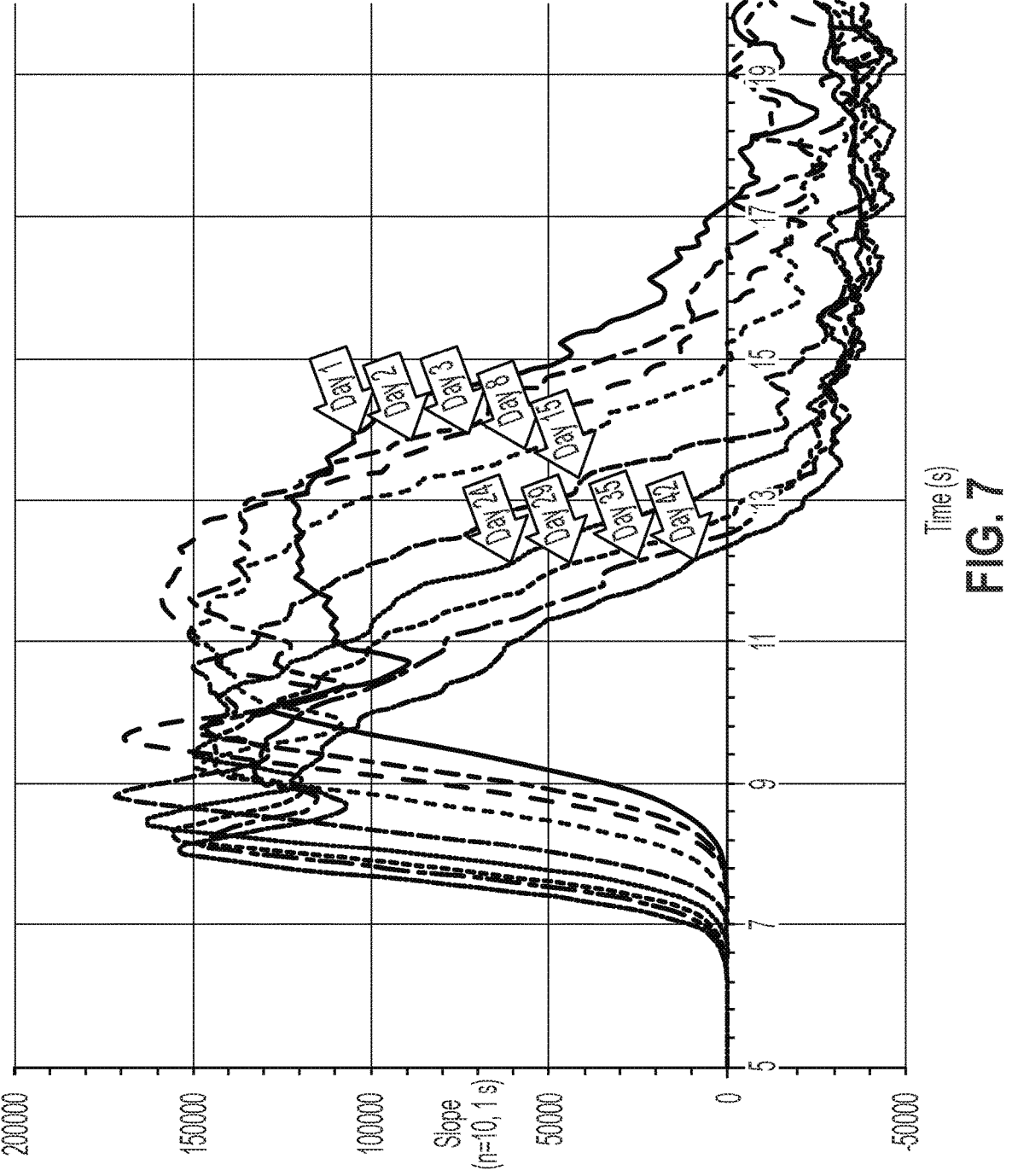
FIG. 7 is a plot of the first derivative of the radioactivity data illustrated in FIG. 6. The FIG. 8 is a plot of lapsed time values versus cumulative eluted volume.

FIG. 7 is a plot of the first derivative of the radioactivity data illustrated in FIG. 6. The y-axis on FIG. 7 is the rate of change of radioactivity (in counts per second per second). The time over each elution is plotted on the x-axis.

The data shown in FIGS. 6 and 7 illustrate the shifting profiles of the radioactivity bolus curves over time/successive elutions.

Example 2: Determining a Characteristic of the Bolus Curves Indicative of Breakthrough After generating the radioactivity profile data illustrated in FIGS. 6 and 7, a characteristic indicative of breakthrough of the parent radioisotope (strontium) into the radioactive eluate was determined for each elution. The characteristic measured for the example was lapsed time. The lapsed time was measured between the start of the elution and when the radioactivity of the radioactive eluate was at a peak level for data illustrated in FIG. 6 or when the derivative of the radioactivity of the radioactive eluate was at zero for data illustrated in FIG. 7. The following table illustrates the characteristic indicative of breakthrough for each elution on FIGS. 6 and 7.

| Day Elution Date Generated | Cumulative Volume Eluted | Lapsed time (sec) for FIG. 6 data | Lapsed time (sec) for FIG. 7 data |
|---|---|---|---|
| 1 | 530 | 16.8 | 17.1 |
| 2 | 1061 | 16.5 | 16.3 |
| 3 | 1607 | 15.5 | 15.7 |
| 8 | 2530 | 14.7 | 14.9 |
| 15 | 5132 | 13.6 | 13.8 |
| 24 | 8866 | 13.2 | 13.3 |
| 29 | 10797 | 12.8 | 12.7 |
| 35 | 13263 | 12.2 | 12.5 |
| 42 | 16139 | 12.3 | 12.3 |

Figure 8:
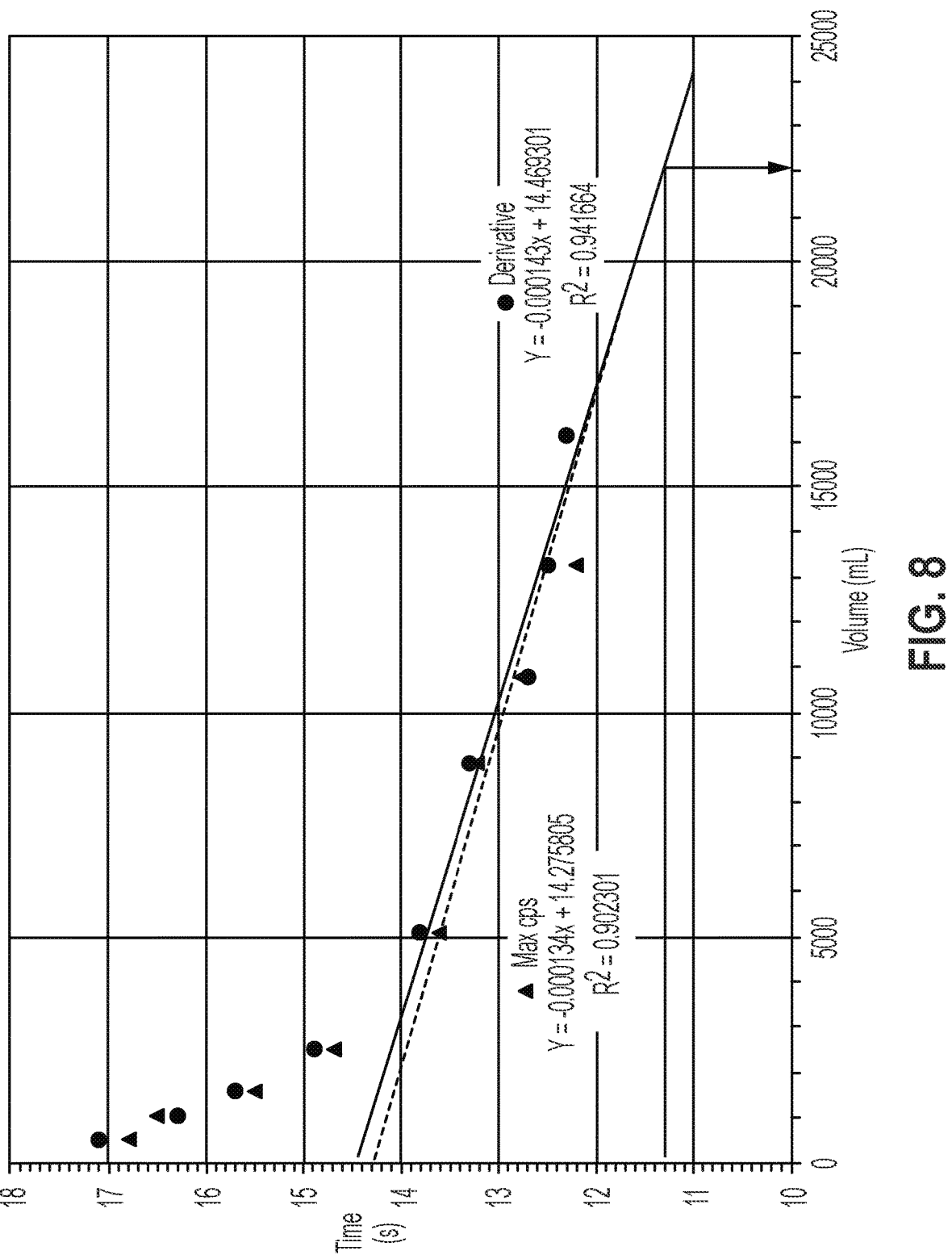

Example 3: Establishing a Predictive Relationship Based on the Breakthrough Characteristic To establish a predictive relationship based on the characteristic (lapsed time) values calculated for the radioactivity profile data in FIGS. 6 and 7 and shown in the Table in Example 2 above, the lapsed time values were plotted against cumulative eluted volume data corresponding to each lapsed time value. A first order curve was fit to the linear region of the plotted data. FIG. 8 is a plot of lapsed time values versus cumulative eluted volume.

For the example dataset of FIG. 6, a curve having the formula $Y=-0.000143x+14.469$ was fit to the linear region of the data. For the example dataset of FIG. 7, a curve having the formula $Y=-0.000134x+14.276$ was fit to the linear region of the data. In the equations, Y is the lapsed time value and X is the cumulative eluted volume value.

Example 4: Predicting how Much More Volume can be Eluted Until Breakthrough

After developing the curve relationship between the characteristic indicative of breakthrough (lapsed time) and cumulative eluted volume as discussed in Example 3, the relationship was used to predict the amount of eluate that can be produced by the generator before breakthrough may be likely to occur. Through separate testing, the radioisotope generator used in the Examples was eluted until breakthrough was observed to occur. The radioactivity profile of the eluate at breakthrough exhibited a lapsed time (between zero activity and max activity) of 11.3 seconds. This 11.3 second value was subsequently used as a breakthrough characteristic (lapsed time).

In this example, the cumulative eluted volume at breakthrough was calculated using the equations discussed in Example 3 above with a lapsed time at breakthrough of 11.3 seconds. The actual volume eluted for each radioactivity profile was then subtracted from the calculated volume at breakthrough to provide a prediction of the remaining volume that can be eluted using the generator before breakthrough is likely to occur. The following table provides calculated values for the remaining volume of eluate that may be eluted from the generator before breakthrough is likely to occur after each successive elution discussed in Example 1.

| Day Elution Date Generated | Cumulative Volume Eluted | mL of Eluate that can be generated prior breakthrough (based on FIG. 6 data and equation) | mL of Eluate that can be generated prior breakthrough (based on FIG. 7 data and equation) |
|---|---|---|---|
| 1 | 530 | 21633 | 21678 |
| 2 | 1061 | 21102 | 21147 |
| 3 | 1607 | 20556 | 20601 |
| 8 | 2530 | 19633 | 19678 |
| 15 | 5132 | 17031 | 17076 |
| 24 | 8866 | 13297 | 13342 |
| 29 | 10797 | 11366 | 11411 |
| 35 | 13263 | 8900 | 8944 |
| 42 | 16139 | 6024 | 6068 |

The invention claimed is:

1. An elution system comprising:
a radioisotope generator configured to release a radioactive eluate containing a daughter radioisotope during an elution with an eluant, the daughter radioisotope being produced from radioactive decay of a parent radioisotope contained within the radioisotope generator;
an eluate tubing line in fluid communication with the radioisotope generator;
a radioactivity detector positioned to detect a radioactivity of the radioactive eluate while the radioactive eluate is flowing through the eluate tubing line; and
a controller communicatively coupled to the radioactivity detector and configured to:
   receive data indicative of the radioactivity of the radioactive eluate generated during the elution thereby providing a radioactivity profile of the radioactive eluate relative to at least one of a time during the elution and a volume of radioactive eluate generated during the elution, and
   determine a characteristic of the radioactivity profile indicative of breakthrough of the parent radioisotope into the radioactive eluate.

2. The system of claim 1, wherein the controller is further configured to compare the determined characteristic of the radioactivity profile indicative of breakthrough to a breakthrough threshold for the characteristic.

3. The system of claim 1, wherein the controller is further configured to determine a remaining capacity of the radioisotope generator before breakthrough.

4. The system of claim 1, wherein the controller is further configured to at least one of (1) issue a user alert and (2) not allow a patient infusion, if the determined characteristic exceeds the breakthrough threshold.

5. The system of claim 4, wherein the controller is further configured to determine a remaining capacity of the radioisotope generator before breakthrough and provide a user alert indicative of the remaining capacity.

6. The system of claim 1, wherein the characteristic of the radioactivity profile indicative of breakthrough of the parent radioisotope into the radioactive eluate comprises a lapsed time or a lapsed volume during the elution between when the radioactivity of the radioactive eluate, or a derivative thereof, is at a first predetermined level and when the radioactivity of the radioactive eluate, or a derivative thereof, is at a second predetermined level.

7. The system of claim 6, wherein the derivative of the radioactivity of the radioactive eluate is a first derivative of the radioactivity of the radioactive eluate over the lapsed time or the lapsed volume, wherein the first predetermined level and the second predetermined level each correspond to a predetermined rate of change of the radioactivity of the radioactive eluate over time or volume.

8. The system of claim 6, wherein the derivative of the radioactivity of the radioactive eluate is a second derivative of the radioactivity of the radioactive eluate over the lapsed time or the lapsed volume, wherein the first predetermined level and the second predetermined level each correspond to a predetermined rate of change of a first derivative of the radioactivity of the radioactive eluate over time or volume.

9. The system of claim 6, wherein the first predetermined level is a zero value.

10. The system of claim 1, wherein the characteristic of the radioactivity profile indicative of breakthrough of the parent radioisotope into the radioactive eluate comprises a lapsed time or a lapsed volume during the elution between a start of the elution and when the radioactivity of the radioactive eluate, or a derivative thereof, is at a second predetermined level.

11. The system of claim 10, wherein the second predetermined level is a maximum radioactivity of the radioactive eluate.

12. The system of claim 1, wherein the radioactivity profile is relative to the time during the elution, the time during elution being a cumulative time from a start of a pump pumping the eluant through the radioisotope generator.

13. The system of claim 1, wherein the radioactivity profile is relative to the volume during the elution, the volume during elution being a cumulative volume from a start of a pump pumping the eluant through the radioisotope generator.

14. The system of claim 1, wherein the radioactivity detector comprises a beta detector or a gamma detector.

15. The system of claim 1, further comprising a base frame with wheels, wherein the radioisotope generator and the radioactivity detector are mounted on the base frame so as to be movable.

16. The system of claim 1, further comprising a shielding assembly providing a barrier to radioactive radiation, wherein the radioisotope generator is contained in the shielding assembly.

17. The system of claim 1, further comprising:
an eluant reservoir containing the eluant;
a pump coupled to the eluant reservoir via an eluant line;
a waste container; and
a plurality of tubing lines including an infusion tubing line, an eluate line, and a waste line, wherein the infusion tubing line is in selective fluid communication with the eluate line and the waste line is in selective fluid communication with the eluate line,
wherein the radioactivity detector is positioned to measure the radioactivity from the radioactive eluate flowing through the eluate line, and
the controller is further configured to determine a remaining capacity of the radioisotope generator before breakthrough based on the determined characteristic of the radioactivity profile indicative of breakthrough.

18. The system of claim 17, wherein the controller is configured to control the pump to pump the eluant through the radioisotope generator, thereby producing the radioactive eluate.

19. The system of claim 17, wherein:
the controller is communicatively coupled to one or more valves and configured to control a flow from the eluate line to a select one of the infusion tubing line and the waste line via the one or more valves; and
the controller is further configured to:
control the pump to pump the eluant through the radioisotope generator and generate the radioactive eluate,
determine the radioactive activity of the radioactive eluate based on radioactivity emissions measured via the radioactivity detector while the radioactive eluate is directed to the waste container,
upon the radioactive activity of the radioactive eluate reaching a threshold level of, control the one or more valves to place the infusion tubing line in fluid communication with the eluate line,
further control the pump to cause eluate to flow through the infusion tubing line,
control the radioactivity detector to continue measuring the radioactivity of the radioactive eluate while the radioactive eluate flows through the infusion tubing line.

20. The system of claim 1, wherein the radioisotope generator is a $^{82}Sr/^{82}Rb$ generator.

* * * * *